United States Patent [19]

Smolin

[11] 4,409,819

[45] Oct. 18, 1983

[54] METHOD OF DETERMINING, AS A PROPERTY OF AN ADSORBENT, THE SELECTIVITY FOR ONE COMPONENT OF A LIQUID CHARGE COMPOSITION WITH RESPECT TO A REFERENCE COMPONENT OF SAID CHARGE COMPOSITION

[75] Inventor: William Smolin, Fishkill, N.Y.

[73] Assignee: Texaco Inc., White Plains, N.Y.

[21] Appl. No.: 378,162

[22] Filed: May 14, 1982

Related U.S. Application Data

[62] Division of Ser. No. 152,865, May 23, 1980, Pat. No. 4,351,981.

[51] Int. Cl.³ ............................................ G01N 33/00
[52] U.S. Cl. ................................................. 73/61.1 R
[58] Field of Search ............................. 73/61.1 R, 53

[56] References Cited

U.S. PATENT DOCUMENTS 3,605,501  9/1971  Chenevert ........................... 73/53 X
4,069,172  1/1978  Kanaoka et al. ................. 252/455 Z Primary Examiner—James J. Gill
Assistant Examiner—Joseph W. Roskos
Attorney, Agent, or Firm—Carl G. Ries; Robert A. Kulason; Carl G. Seutter

[57] ABSTRACT

An adsorbent may be tested at ambient temperature to determine its selectivity for one component of a charge liquid composition with respect to a reference component of the charge composition by equilbration at ambient temperature in the presence of an essentially inert liquid charge; the results determined at e.g. room temperature of e.g. 70° F. are found to permit separation of xylenes at elevated temperatures of typically 340° F.

3 Claims, 6 Drawing Figures

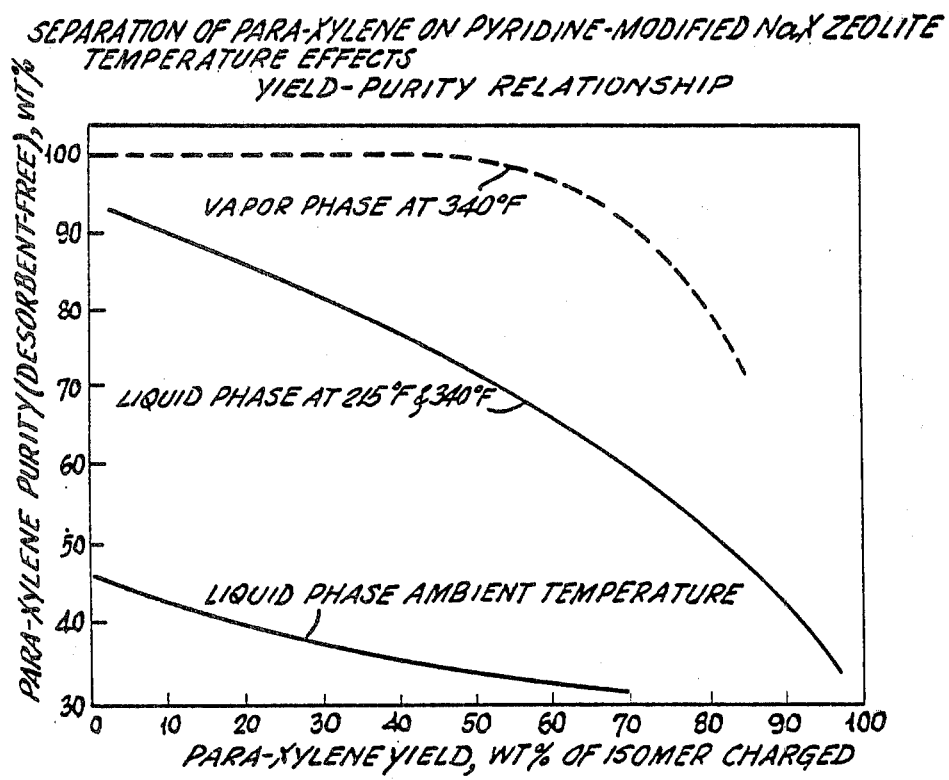
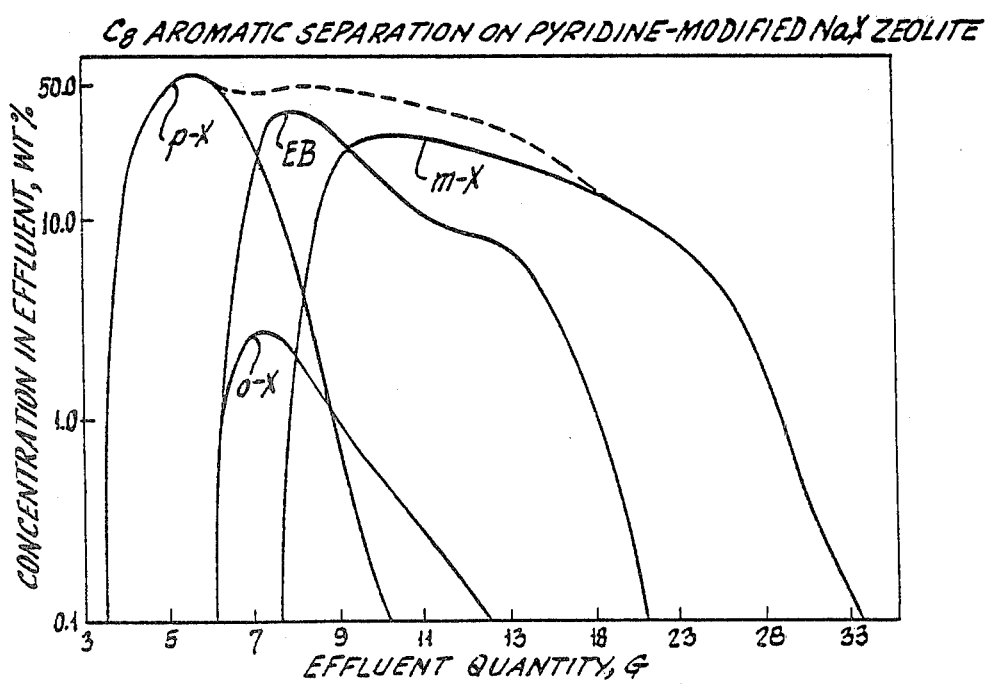

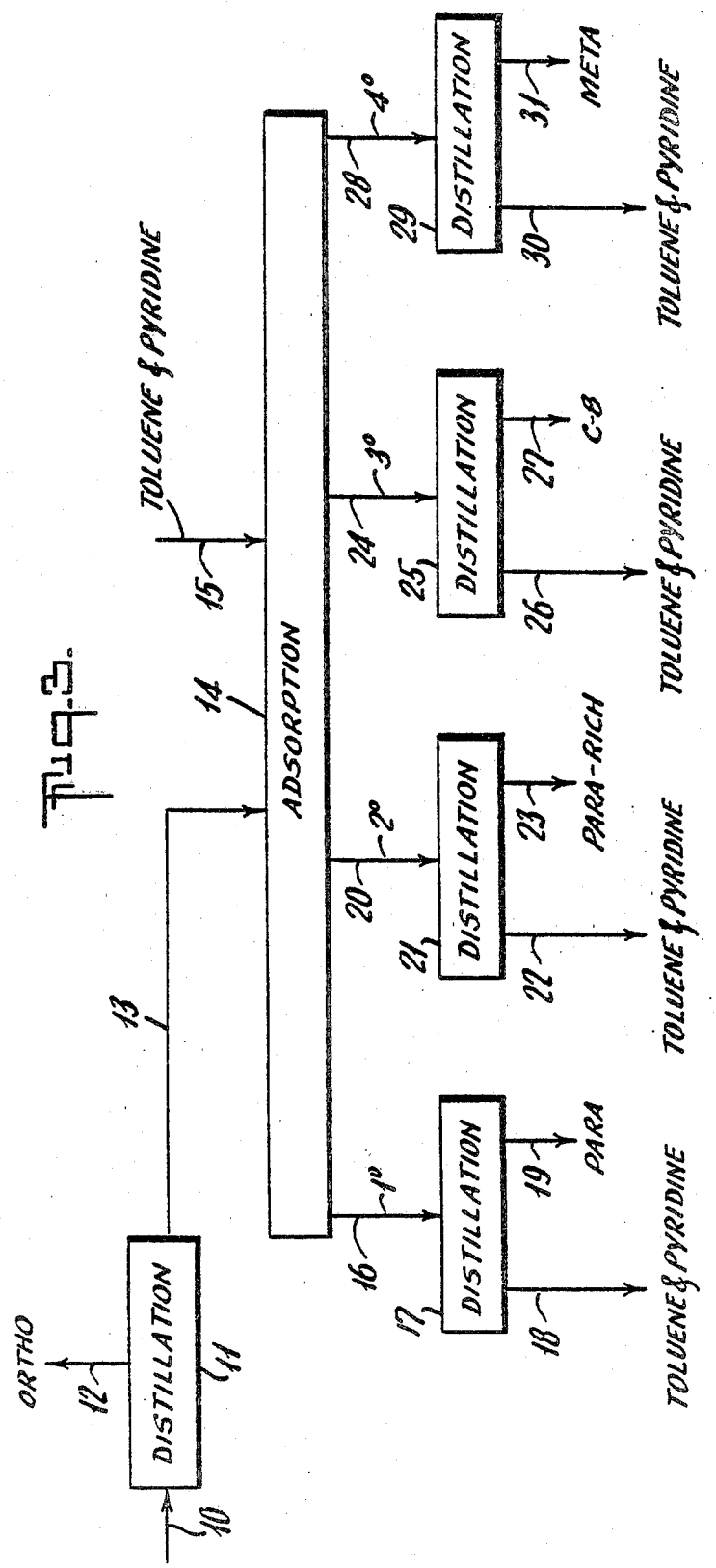

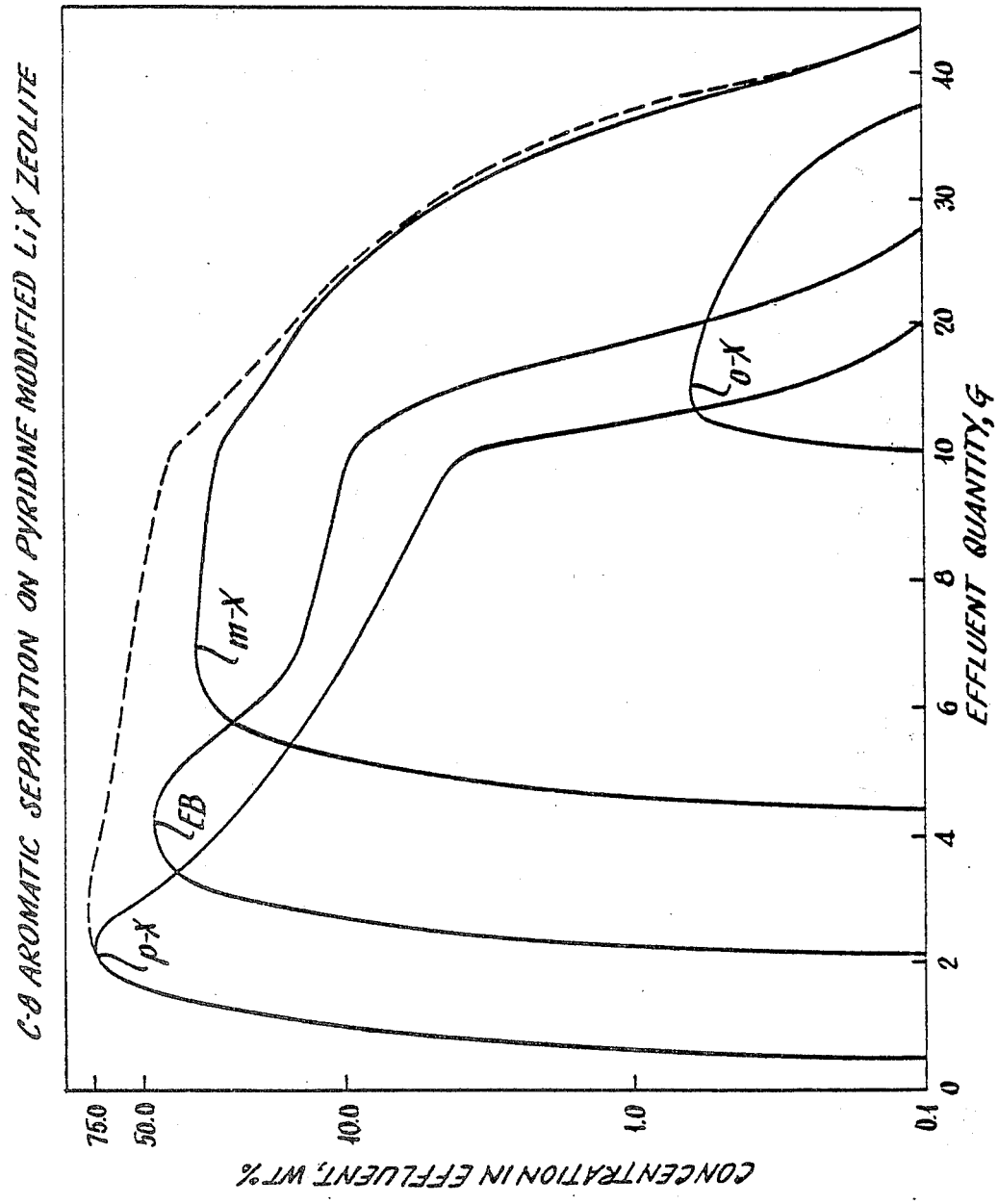

METHOD OF DETERMINING, AS A PROPERTY OF AN ADSORBENT, THE SELECTIVITY FOR ONE COMPONENT OF A LIQUID CHARGE COMPOSITION WITH RESPECT TO A REFERENCE COMPONENT OF SAID CHARGE COMPOSITION

RELATED APPLICATION

This is a division of application Ser. No. 152,865 filed May 23, 1980, now U.S. Pat. No. 4,351,981 issued Sept. 28, 1982.

FIELD OF THE INVENTION

This invention relates to solid-bed adsorptive separation. More particularly, it relates to the separation of p-xylene from C-8 aromatic hydrocarbon streams as a least strongly adsorbed, or front end, product.

DESCRIPTION OF THE PRIOR ART

Solid bed adsorption techniques have been used to separate individual hydrocarbon isomers from charge hydrocarbon streams typified by C-8 aromatic streams containing ethylbenzene and xylene isomers.

Separation of para-xylene from other charge streams has been described in U.S. Pat. Nos. including: 3,558,730, 3,558,732, 3,626,020, 3,663,638, 3,734,924.

In these illustrative patents, particular zeolites may be used to selectively adsorb para-xylene from feed mixtures which contain several C-8 aromatic isomers; and in these patents the p-xylene is selectively adsorbed and is ultimately recovered as a tail-end or extract product while the remaining xylenes and ethylbenzene are recovered as front-end or raffinate components.

In other patents, typified by U.S. Pat. No. 3,997,619, there are disclosed processes for recovering ethylbenzene wherein this component is relatively unadsorbed and is thus recovered as high purity front-end product, the xylene isomers being recovered as tail-end products—this being effected by use of an adsorbent which is "all xylene" selective.

It is an object of this invention to provide a process for separating p-xylene as front-end or raffinate product from a C-8 charge stream. Other objects will be apparent to those skilled in the art.

STATEMENT OF THE INVENTION

In accordance with certain of its aspects, this invention is directed to a process for separating para-xylene from a feed mixture containing C-8 aromatic hydrocarbon including para-xylene which comprises contacting said feed mixture with, as an adsorbent, a pyridine-modified sodium X or lithium X zeolite thereby adsorbing substantially all of said C-8 aromatic hydrocarbon to the substantial exclusion of para-xylene; and recovering said para-xylene.

DESCRIPTION OF THE INVENTION

The charge mixtures which may be treated by the process of this invention include mixtures containing C-8 aromatic hydrocarbons including para-xylene. These mixtures, which contain substantial quantities of ethylbenzene and the xylene isomers, generally are produced by reforming and isomerization processes which are well known to the refining and petrochemical arts. In reforming processes, a naphtha feed may be contacted with a platinum-halogen-containing catalyst at severities selected to produce an effluent containing C-8 aromatic isomers. Generally the reformate is then fractionated to concentrate the C-8 aromatic isomers in a C-8 fraction. The C-8 aromatic isomers may then be further concentrated by solvent extraction processes. Xylene isomerization processes isomerize at isomerization conditions a xylene mixture which is deficient in one or more isomers to give an effluent containing approximately equilibrium quantities of the C-8 aromatic isomers. The equilibrium compositions of the xylene isomers and ethylbenzene at various temperatures are shown in the Table below.

TABLE

| EQUILIBRIUM C-8 AROMATIC COMPOSITIONS* | | | |
|---|---|---|---|
| Temperature °F. | 620 | 800 | 980 |
| | Mole percent of isomers | | |
| Ethylbenzene | 6 | 8 | 11 |
| Para-xylene | 22 | 22 | 21 |
| Meta-xylene | 50 | 48 | 45 |
| Ortho-xylene | 22 | 28 | 23 |

*Based on API sources

Feed stream may contain ethylbenzene and any of the xylene isomers in addition to para-xylene. Extracted C-8 reformate fractions and isomerates from xylene isomerization processes containing all of the xylene isomers can be charged as feed streams. Feed streams include effluent streams from processes which have removed varying amounts of one or more xylene isomers or ethylbenzene. As an example, at least a portion of the ortho-xylene may have been previously removed by fractionation from a feed mixture containing the xylene isomers. Ortho-xylene has a boiling point of about 6° F. higher than that of the nearest other C-8 aromatic (meta-xylene) and hence can be removed as a bottoms product from ortho-xylene fractionator towers. The concentration of ortho-xylene in the effluent from this fractionation process which can be used as a feed stream may be less than the concentrations of either para-xylene or meta-xylene.

Ethylbenzene, which has a lower boiling point than any of the xylene isomers, may also be separated by distillation, preferably after removal of at least a portion of the ortho-xylene. The concentration of ethylbenzene in the effluent from this fractionation process which can be used as a feed stream may be less than the concentrations of either para-xylene or meta-xylene. Removal of ethylbenzene and/or ortho-xylene from C-8 aromatic mixtures may be effected by distillation.

C-8 aromatic components, other than those desired as product, should be present in the feedstock at as low a concentration level as possible. Thus for para-xylene production, the content of meta-xylene, ortho-xylene, and ethylbenzene should be as low as possible. For production of both para-xylene and meta-xylene, it is desirable to maintain the content of ortho-xylene and ethylbenzene as low as possible. In practice, only ortho-xylene and ethylbenzene can be removed by distillation, so a charge stock containing a concentrate of meta-xylene and para-xylene would be typically available for production of either para-xylene or para-xylene and meta-xylene. It is to be noted that separation of ethylbenzene by distillation is expensive; and accordingly economic considerations may dictate that the feedstock would have been treated in manner to principally reduce the content or ortho-xylene.

In accordance with practice of the process of this invention, the feed mixture containing C-8 aromatic hydrocarbon including para-xylene may be contacted with, as an adsorbent, a pyridine-modified sodium X or lithium X zeolite, thereby selectively adsorbing substantially all of said C-8 aromatic hydrocarbon to the substantial exclusion of para-xylene.

The NaX-type zeolite which may be used in the process of this invention may include those which contain 77 up to 96 aluminum atoms in the unit cell and which have an atom ratio of silicon-to-aluminum of greater than 1.00.

A NaX-type zeolite may be represented by the formula:

$$Na_a[(AlO_2)_a(SiO_2)_b]cH_2O$$

wherein a plus b equals 192; a is 77–96; and c is commonly 264 in the hydrated state. A typical NaX-type zeolite has the formula:

$$Na_{86}[(AlO_2)_{86}(SiO_2)_{106}]0.264H_2O$$

NaX zeolites are well known to those skilled in the art (qv U.S. Pat. No. 3,997,619 inter alia) and may be available from various sources or may be readily prepared.

LiX zeolites may be available commercially or may be prepared by exchanging an NaX zeolite with aqueous solution containing lithium ions—typically lithium acetate.

It has been found that, although it may be convenient to utilize the "standard" sodium zeolite supra, the process of this invention using a pyridine modified sodium zeolite may function at greater efficiency if the atom ratio of silicon-to-alumina is somewhat greater than for the standard which has an atom ratio of ca 1.22. The instant process may utilize high-silica NaX-type zeolites having a ratio of 1.22–1.50, typically 1.44.

The high-silica NaX-type zeolites may have a ratio of 1.22–1.50, say 1.44.

In this instance, the typical formula might be:

$$Na_{79}[(AlO_2)_{79}(SiO_2)_{113}]0.264H_2O$$

In practice of the process of this invention, adsorption is effected in the presence of a pyridine. Although it may be possible to obtain separation of para-xylene by the use of other pyridines, such as the picolines (including 2-picoline or 3-picoline, or 4-picoline), or the lutidines (including 2, 4-lutidine or 2,6-lutidine, or 3,4-lutidine), it is found that most effective operation may be achieved by the use of pyridine se; quinolines (quinoline se and isoquinoline) afford little or no improvement over the unmodified zeolite.

The organic modifier (preferably pyridine) may be present during adsorption in amounts of about 10%–60% of the total adsorptive capacity (C-8 aromatic plus modifier) of the zeolite. The capacity of NaX-type zeolite, expressed as weight % of adsorbed component(s) relative to weight of dry adsorbent, may typically be 10–25 with many NaX-type zeolites falling in the 13–21 range. Total capacity may be essentially equivalent for C-8 aromatics, pyridine, and their mixtures. The pyridine loading is typically in the range of 1–20 wt. %, preferably 3–6 wt. %, say about 4 wt. % of the amount of zeolite adsorbent.

Thus, the weight ratio of pyridine to total capacity of the zeolite may be of the order of 0.1–0.6 or more, say 0.2–0.5.

A typical instance may utilize a pyridine loading of 6.0% (of the adsorbent) where the adsorbent may have a total capacity of 17.6% corresponding to a ratio of 0.34.

In the preferred embodiment, the pyridine is loaded onto the zeolite adsorbent prior to initiation of operation; and this may commonly be effected by contacting the pyridine modifier with the adsorbent before the latter is admitted to the reaction vessel. Preferably, the modifier is mixed with, or dissolved in, the desorbent to be used in the process as hereinafter described and the adsorbent is submerged in the mixture. At room temperature, pyridine is substantially completely removed from solution by the zeolite.

The adsorbent can be contained in one or more chambers where through programmed flow into and out of the chamber separation of the isomers is effected. Preferably in operation, fixed quantities of a charge stream and of a desorbent stream are admitted alternately to one end of a bed or column of zeolite; and effluent from the other end of the column is segregated into cuts. The bed may be operated in either up-flow or down-flow mode. Concentrations of individual charge components and of desorbent in effluent from the columns resulting from this operation vary with time (or quantity of total effluent). FIGS. 2 and 4 illustrate the manner in which this composition variation occurs for two specific cases. The resolution of components taking place in the column is characterized as a cyclic, chromatographic, adsorptive separation where the cycle time is the interval between the start of introduction of corresponding successive portions of charge (or of desorbent) to the column, or their appearance in the effluent. Effluent from the column during each cycle is segregated into fractions, or cuts, which may include (1) a front end cut taken at the beginning of the cycle in which the least strongly adsorbed charge component (para-xylene) is concentrated to high purity relative to other charge components; (2) a back end or tail-end cut taken at the end of the cycle in which the most strongly adsorbed charge component (meta-xylene) is concentrated to high purity relative to other charge components; (3) one or more intermediate cuts in which either the front end or back end product component is concentrated relative to other charge components, but at a lower purity level than in the produce cut (such cuts may be recycled to the charge preparation operation to permit substantially complete recovery of product component(s) in high purity); and (4) one or more cuts in which only small amounts of product components(s) are present. If desired, cut (2) or cut (3), or both, may be combined with cut (4).

The cyclic process may be carried out either in the liquid phase or in the vapor phase. Liquid phase operation may be carried out at lower temperatures and may permit easier control of charge and cut points, but vapor phase operation is preferred because of the much greater separation efficiency afforded by this mode. Preferred conditions for the process of this invention in liquid phase operation will include temperatures within the range from about 100° to about 450° F. at pressures sufficient to maintain a liquid phase and to provide a driving force for moving fluid through the adsorbent bed, generally in the range from about atmospheric to about 500 psig. Preferred conditions for the process of this invention in vapor phase operation will include temperatures from about 290° F. to about 450° F. sufficient to maintain components in the vapor phase at pressures from about atmospheric to about 80 psig, the pressure preferably being the minimum required to drive fluid through the system.

In both liquid and vapor phase modes, operation is substantially isothermal; and pressure drop across the system is substantially constant, although some variation may occur during the course of a cycle. The quantity of desorbent introduced for a given quantity of charge is sufficient to displace all charge components to an extent that the residual total charge component concentration in the effluent for a given cycle is very low, preferably below about 0.1%, before charge components from the following cycle start to appear. This determines the minimum preferred desorbent: charge ratio; if less desorbent is used, product purity in subsequent cycles is reduced. If more desorbent is used, separation is still achieved, but the cycle time and amount of desorbent to be removed from product fractions are unnecessarily increased. The quantity of charge introduced per cycle and the minimum desorbent: charge ratio for this quantity of charge are related to a number of factors including adsorbent capacity, selectivity, and particle size, fluid flow rate, and particularly to charge composition and to column length. Preferred process design specifications are largely related to the cost of the absorbent bed per unit of pure product production rate and to the cost of separating desorbent from effluent fractions; both costs must be considered together.

The process of this invention may also be effected in a simulated moving bed countercurrent system. The operating principles and sequence of such a flow system are described in U.S. Pat. No. 2,985,589 issued to D. B. Broughton which patent is incorporated herein by specific reference thereto. This system may be operated in the liquid phase mode with the same pyridine-modified zeolite adsorbent and in the same temperature and pressure ranges as those previously described for cyclic operation in the liquid phase mode. Para-xylene is recovered as at least strongly adsorbed, or raffinate product. In this system however, only a single pure product may be recovered; and a separate, additional system would be required to recover both para-xylene and meta-xylene products. Operation of a simulated moving bed countercurrent system in the vapor phase mode, while possible in principle, would be difficult to achieve in practice; so if the advantageous separation efficiency of the vapor phase mode is to be obtained, the cyclic operating procedure is preferred.

The desorbent materials which are used in the preferred processing schemes employed may vary depending on the type of operation employed. The term "desorbent material" as used herein means any fluid substance capable of removing a selectively adsorbed feed component from the adsorbent. In the swing-bed system, in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated at substantially constant pressures and temperatures, and desorbent material relied upon must by judiciously selected to satisfy several criteria. First, the desorbent material must displace the adsorbed feed component from the adsorbent with reasonable mass flow rates without itself being so strongly adsorbed as to unduly prevent charge components from displacing the desorbent material in a following adsorption cycle. Secondly, desorbent materials must be compatible with the particular adsorbent and the particular feed mixture. More specifically, they must not reduce or destroy the critical selectively of the adsorbent for the components of the charge.

Desorbent materials to be used in the process of this invention should additionally be substances which are easily separable from the feed mixture that is passed into the process. Each of the effluent cuts in cyclic processes, and both raffinate and extract streams in simulated moving bed countercurrent processes, contain desorbent in admixture with charge components. Without a method such as distillation, for separating desorbent material the product purity would be low; and consumption of desorbent in the process would be excessive. Any desorbent material used in this process will have a substantially different average boiling point from that of the feed mixture. The use of desorbent material having a substantially different average boiling point than that of the feed allows separation of desorbent material from feed components in the various effluent cuts or the extract and raffinate streams by fractionation thereby permitting reuse of desorbent material in the process. The term "substantially different" as used herein means that the difference between the average boiling points between the desorbent material and the feed mixture shall be at least 15° F. The boiling range of the desorbent material may be higher or lower than that of the feed mixture.

Among the desirable characteristics of an adsorbent are: adsorptive capacity for some quantity of an extract component per unit quantity of adsorbent; the selective adsorption of feed components with respect to one another such that a desired pure product component is adsorbed more strongly or less strongly than the other components; and sufficiently fast rates of adsorption and desorption of the extract components to and from the adsorbent.

Capacity of the adsorbent for adsorbing components of the separation system, including desorbent, is, of course, a necessity; without such capacity the adsorbent is useless for adsorptive separation. Increased capacity of a particular adsorbent makes it possible to increase the separation efficiency and thereby reduce the amount of adsorbent needed to effect separation of a particular feed mixture at a given produce purity and yield. (Yield is defined as the fraction of a feed component recovered as pure product.) A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity for one component as compared to another component. Relative selectivity can be expressed not only for one feed component as compared to another but can also be expressed between any feed mixture component and the desorbent material. The selectivity as used throughout this specification is defined as the ratio of concentrations of the two components in the adsorbed phase divided by the ratio of concentrations of the same two components in the unadsorbed phase at equilibrium conditions.

Determining these adsorbent characteristics, particularly capacity and selectivities for charge and desorbent components, is essential for developing an adsorptive separation system for recovering specific pure components from mixtures with difficulty separable substances, such as isomers of the desired products. Further, once such a system is established, a convenient test method is required for determining that subsequent batches of adsorbent are equivalent to the original adsorbent or fall within a satisfactory range. I have found a convenient and effective procedure for accomplishing these objectives which comprises the steps of:

(1) Combining a suitably prepared (i.e. dried to a specific moisture level) adsorbent sample with a test mixture of test components, which may include components of a mixture to be separated, desorbent materials, and adsorbent modifiers, in the presence of a reference component which is essentially unadsorbed and essentially inert, in the presence of strongly adsorbed test components. For determining adsorption equilibria for mixtures of aromatic hydrocarbons, paraffinic or cycloparaffinic hydrocarbons are suitable reference components. A particularly suitable reference component is cyclohexane.

(2) Equilibrating the solid-liquid mixture with suitable agitation in a sealed vessel at a convenient temperature, which may be room temperature.

(3) Separating equilibrated liquid from solid adsorbent (eg by centrifuging), sampling the liquid, and analyzing the liquid by a suitable procedure (eg gas chromatography) for determining the concentration of each of the components present.

(4) From the known weight and composition of the test component-reference component test mixture charged, and composition of equilibrium liquid, calculating the quantity of each test component in the equilibrium liquid using as a basis for such calculation the originally charged weight of inert (nonadsorbed) reference component in both the test liquid and equilibrium liquid.

(5) By difference, from the calculated weight of each component in the equilibrium liquid and the known amount of each component in the charge, calculating the weight of each test component adsorbed.

(6) From the weight of adsorbent charged and the weights of test components adsorbed, calculating the capacity of the adsorbent for the test components and the composition of the adsorbed phase.

(7) From the calculated composition of the adsorbed phase and the composition of the equilibrium liquid phase obtained by analysis, determining selectivity of the adsorbent for any pair of test components.

The method may be used to screen separation systems prior to column operation; separation obtained from column operation at elevated temperature are found to correspond to those expected from the adsorbent characteristics determined by the test method. It may be used to determine variation of selectivity with fluid phase composition, a relationship not readily obtainable from other methods for estimating adsorbent selectivities. It may be used to determine the effects of components added to modify the selectivity characteristics of original adsorbents or to determine the effects of impurities (such as water) which may be present in charge or desorbent streams, particularly in commercial operation. It may be used to determine variations of adsorbent capacity, which may be due to occluded solid material in the pores or to variations in the quantity of binder used, which do not appreciably affect adsorbent selectivity. It may be used as an adsorbent specification test where specific values or ranges of capacity and selectivity for specific test components at particular concentration levels are specified. It may be used to select suitable desorbent materials. It may also be used as a control test during manufacture of zeolites.

The preferred desorbent may be toluene. Benzene may be employed as desorbent. Naphthalene is too strongly adsorbed; and 1,3-diethylbenzene is too weakly adsorbed to be of interest. 1-methyl naphthalene may be employed in the separation of para-xylene if the feed or charge stream is free of ortho-xylene.

In isothermal, isobaric, operation of the process of my invention, I have found that desorbent materials comprising mono-aromatic hydrocarbons are particularly effective. Specifically, desorbent materials comprising toluene are preferred for this type of operation.

In operation of the process of this invention in the cyclic, liquid phase mode, the pyridine-loaded zeolite, packed in the adsorption column, is flooded with desorbent toluene which is passed downwardly through the adsorbent bed at a flow rate of 0.1-6, say about 2 gallons per minute per square foot of column cross section. Periodically the flow of toluene is interrupted and a portion of charge is introduced at about the same flow rate. Pyridine is preferably added with the desorbent toluene to balance pyridine removed from the adsorbent bed in the column effluent; the amount added depends on the pyridine loading of the adsorbent and the temperature of the adsorption column—typically it may be 0.01%-1.0%, say 0.2% of the desorbent toluene. As the effluent is monitored (by gas chromatography, for example), toluene desorbent is first observed. When the first C-8 component shows, which in this process is para-xylene, the cycle is considered started.

It is possible to collect incremental portions of product (over equal time increments), but preferred operation is carried out by collecting the entire yield of high purity (i.e. 99+% purity) para-xylene in one aliquot. Depending on the details of the downstream processing facility, there may be recovered a second produce stream which is rich in paraxylene although it is of a purity less than that of the first product stream. A third stream may be recovered which contains a mix of C-8 components. A last stream may be recovered containing substantially pure meta-xylene.

Each of these product streams may be separated, as by distillation, from the toluene and pyridine. Pyridine and toluene are recovered together and may be recycled.

Operation in the vapor phase is comparable. The adsorbent may be loaded with pyridine and toluene in liquid phase ab initio. The system is then heated to e.g. 340° F. and liquid displaced from the column by passing vapor phase toluene desorbent (containing added pyridine) downwardly through the adsorbent bed. Charge is introduced periodically in the vapor phase. The effluent is condensed and collected in desired increments followed by recovery of the desired high purity para-xylene from toluene and pyridine in the front end product and, in some cases, high purity metaxylene as a back end product.

ADVANTAGES OF THE INVENTION

It is a feature of the process of this invention that it is characterized by many advantages including the following:

(i) it permits attainment of p-xylene as a front-end product which is typically more easily purified than is the tail-end product, and which may be recovered as product having a very low level of C-8 impurities;

(ii) it permits operation under conditions of high selectivity;

(iii) selectivity increases as the concentration of less strongly adsorbed component increases, and thus operation at the front-end of the adsorption cycle permits higher selectivity to be realized as the proportion of p-xylene in C-8 aromatics increases in this portion of the cycle;

(iv) the content of impurities, originating from the tail of a preceding cycle, is measured against a high front-end product peak and, even under the least favorable conditions of operation, causes a smaller loss of product purity than would the internal front end components tailing into a back end product; and (v) a second high purity product (m-xylene) may be obtained as a back-end or tail-end product with little modification of the p-xylene recovery system.

DESCRIPTION OF THE DRAWINGS

FIG. 1 presents illustrative curves, for operation in liquid and vapor phase, showing the purity of para-xylene in a recovered cut as a function of the para-xylene yield, expressed in terms of the percent recovery of para-xylene basis para-xylene charged for a pyridine-modified NaX zeolite;

FIG. 2 presents illustrative curves showing the concentration in the effluent of specific isomers as a function of effluent quantity for a pyridine-modified NaX zeolite;

FIG. 3 presents a schematic process flow sheet showing operation according to one embodiment of the process of this invention;

FIG. 4 presents illustrative curves (otherwise comparable to those of FIG. 2) for a pyridine-modified LiX zeolite;

DESCRIPTION OF PREFERRED EMBODIMENTS

Figure 6:
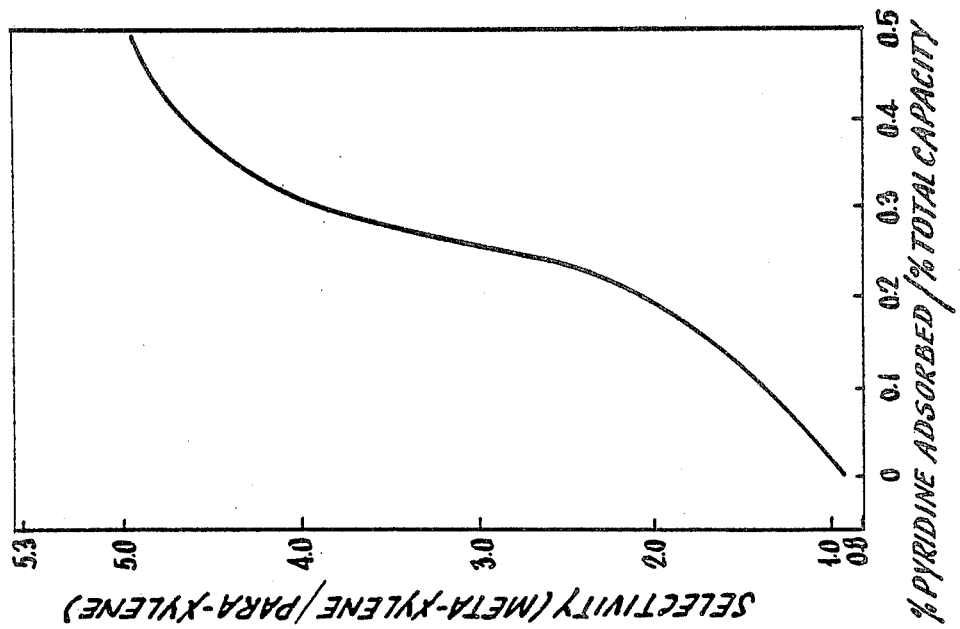
FIG. 6 presents an illustrative curve similar to that of FIG. 5 except showing Selectivity of meta-xylene/para-xylene as a function of the ratio of % pyridine adsorbed/% total capacity.

Practice of the novel process of this invention may be apparent to those skilled in the art from the following description of various embodiments wherein as elsewhere in the description, all parts are parts by weight unless otherwise specified.

EXAMPLES 1-33

In these examples, equilibrium data were obtained for adsorption of C-8 aromatic isomers on various sodium X zeolite samples both in their original form and modified by the addition of pyridine.

Adsorbents used were dried in a tube furnace under a flow of dry nitrogen, then were loaded into previously weighed glass ampoules in a nitrogen-flushed dry box. The weight of adsorbent was determined, then a quantity of previously prepared charge mixture was introduced, the ampoule was chilled in liquid nitrogen, evacuated, sealed, and weighed to determine the weight of charge mixture. Charge mixtures were made up with known amounts of C-8 aromatics, inert reference component (cyclohexane), and pyridine. In other examples (eg Examples 63–70), a desorbent component was included and, in some cases (eg Examples 37–38), a different reference component was used; and in some examples (eg Examples 34–46 and 49–52) a different zeolite modifier was used. The ratio of reference component to total C-8 aromatics (and desorbent, if present) was generally 1.0–1.5:1. Pyridine was present in an amount sufficient to give a desired ratio of pyridine/dry adsorbent. The weight ratio of liquid charge to adsorbent was normally about 2 and the quantity of adsorbent used was generally about 1 gram.

Loaded ampoules were agitated on a shaker table at a temperature of about 75° F. for an equilibration period. Typically the equilibrium period was about one week up to several months, but equilibration was probably substantially complete after one to two days. After equilibration, ampoules were usually centrifuged to facilitate separation of liquid from adsorbent, then the liquid was sampled and analyzed by gas chromatography. Replicate analyses were usually obtained and analyses of samples of charge liquid (retained in sealed ampoules) were usually carried out at the same time.

The quantity of each C-8 aromatic (and desorbent, if present) in the equilibrium liquid was calculated from the GC analysis and known weight of reference component in the charge as $$\text{Wt. Component (Equil.)} = \frac{\% \text{ Component (Equil.)}}{\% \text{ Reference (Equil.)}} \times \text{Wt. Reference (Charge)}$$

The corresponding quantity of component adsorbed per unit weight of adsorbent charged was calculated as:

$$\frac{\text{Wt. Component Adsorbed}}{\text{Wt. Adsorbent}} = \frac{\text{Wt. Component (Equil.)} - \text{Wt. Component (Charge)}}{\text{Wt. Adsorbent}}$$

Pyridine loading of the adsorbent (per unit weight of adsorbent) was calculated on the basis of complete pyridine adsorption as:

$$\text{Pyridine Loading} = \frac{\text{Wt. Pyridine (Charge)}}{\text{Wt. Adsorbent}}$$

The gas chromatographic procedure used for sample analysis was not suitable for pyridine analysis, but measured nitrogen concentrations of not more than 1–2 ppm confirmed that the amount of pyridine in the equilibrium liquid was negligible.

Total capacity of the adsorbent is the sum of individual component adsorption values plus the pyridine loading. Component of the C-8 aromatics (and desorbent, if present) in the adsorbent phase is calculated from the individual component adsorption values.

The selectivity with which an adsorbent adsorbs one component relative to another is a measure of its separation capability. Selectivity factors alpha ($\alpha$) are commonly used as measures of adsorbent selectivity between components of a mixture. Selectivity between any two components is defined as:

$$\alpha = \frac{\left(\frac{\text{Conc. Component 1}}{\text{Conc. Component 2}}\right) \text{Adsorbed Phase}}{\left(\frac{\text{Conc. Component 1}}{\text{Conc. Component 2}}\right) \text{Fluid Phase}}$$

Thus $\alpha$ will be greater than 1.0 if component 1 is more strongly adsorbed than component 2. With a multi-component mixture it is convenient to express selectivities of the components relative to a particular component of the mixture.

Selectivity factors in the present examples are calculated from the composition of the adsorbed phase, determined as described above, and the composition of the equilibrium liquid determined by gas chromatography.

In each of Examples 1–33, a charge liquid containing equal portions by weight of ethylbenzene, p-xylene, m-xylene, and o-xylene (plus cyclohexane reference component) was equilibrated against a designated NaX zeolite. When pyridine was present, it is reported as weight percent of adsorbent.

The following table sets forth equilibrium data at 75° F. on various NaX zeolites—both with and without pyridine modifier. The NaX zeolite of Examples 1–4 was activated at 700° F. In Examples 5–8, the charge was the same NaX zeolite which had been activated at 800° F. The remaining examples each used an NaX zeolite from a different lot: (i) Examples 9–13, (ii) Examples 14–18; (iii) Examples 19–23; (iv) Examples 24–28; and (v) Examples 29–33. The NaX zeolites of Examples 1–18 were used without binder; the NaX zeolites of Examples 19–33 were mixed with binder to form a composite containing about 80% NaX zeolite. The Pyridine Loading is expressed as weight percent of the dry adsorbent, as charged. Capacity of the zeolite (total and C-8) is expressed as weight % adsorbed component(s) per unit weight of adsorbent.

There are tabulated the selectivity (alpha) of (i) EB (ethylbenzene) with respect to p-xylene; (ii) P-X (para-xylene) with respect to p-xylene, which is of course 1.00, included for reference; (iii) M-X (meta-xylene) with respect to p-xylene; and (iv) O-X (ortho-xylene) with respect to p-xylene.

TABLE

Equilibrium Data - NaX Zeolites with and without Pyridine Modifier

| Example | Pyridine Loading | Capacity Total | Capacity C-8 | Selectivity EB | Selectivity P | Selectivity M | Selectivity O |
|---|---|---|---|---|---|---|---|
| 1 | 0 | 13.2 | 13.2 | 0.89 | 1.00 | 0.87 | 1.35 |
| 2 | 0 | 13.4 | 13.4 | 0.89 | 1.00 | 0.85 | 1.32 |
| 3 | 2.9 | 13.2 | 10.3 | 1.87 | 1.00 | 2.36 | 1.44 |
| 4 | 5.5 | 13.2 | 7.7 | 2.47 | 1.00 | 3.50 | 1.42 |
| 5 | 0 | 12.3 | 12.3 | 0.88 | 1.00 | 0.84 | 1.34 |
| 6 | 0 | 12.5 | 12.5 | 0.89 | 1.00 | 0.84 | 1.27 |
| 7 | 2.8 | 11.7 | 8.9 | 1.88 | 1.00 | 2.43 | 1.40 |
| 8 | 5.4 | 11.4 | 6.0 | 3.44 | 1.00 | 5.34 | 1.59 |
| 9 | 0 | 22.5 | 22.5 | 0.88 | 1.00 | 0.84 | 1.33 |
| 10 | 0 | 22.6 | 22.6 | 0.90 | 1.00 | 0.84 | 1.33 |
| 11 | 2.7 | 22.7 | 20.0 | 1.26 | 1.00 | 1.43 | 1.24 |
| 12 | 2.8 | 22.4 | 19.6 | 1.25 | 1.00 | 1.44 | 1.19 |
| 13 | 6.1 | 21.6 | 15.6 | 2.75 | 1.00 | 3.48 | 1.44 |
| 14 | 0 | 22.4 | 22.4 | 0.90 | 1.00 | 0.83 | 1.29 |
| 15 | 0 | 22.1 | 22.1 | 0.90 | 1.00 | 0.81 | 1.27 |
| 16 | 2.8 | 22.0 | 19.2 | 1.37 | 1.00 | 1.49 | 1.21 |
| 17 | 2.9 | 22.4 | 19.5 | 1.37 | 1.00 | 1.48 | 1.17 |
| 18 | 5.6 | 22.7 | 17.0 | 2.26 | 1.00 | 2.65 | 1.31 |
| 19 | 0 | 18.6 | 18.6 | 0.87 | 1.00 | 0.93 | 1.25 |
| 20 | 0 | 17.6 | 17.6 | 0.87 | 1.00 | 0.91 | 1.23 |
| 21 | 3.1 | 17.7 | 14.6 | 1.73 | 1.00 | 2.11 | 1.21 |
| 22 | 2.8 | 16.9 | 14.1 | 1.60 | 1.00 | 1.97 | 1.18 |
| 23 | 5.9 | 17.8 | 11.9 | 3.22 | 1.00 | 4.07 | 1.24 |
| 24 | 0 | 17.7 | 17.7 | 0.84 | 1.00 | 0.92 | 1.19 |
| 25 | 0 | 18.0 | 18.0 | 0.84 | 1.00 | 0.91 | 1.17 |
| 26 | 3.2 | 18.1 | 14.9 | 1.70 | 1.00 | 2.14 | 1.08 |
| 27 | 3.2 | 18.6 | 15.4 | 1.65 | 1.00 | 2.10 | 1.11 |
| 28 | 5.9 | 18.6 | 12.6 | 3.29 | 1.00 | 4.13 | 1.08 |
| 29 | 0 | 17.0 | 17.0 | 0.84 | 1.00 | 0.92 | 1.17 |
| 30 | 0 | 16.6 | 16.6 | 0.84 | 1.00 | 0.91 | 1.14 |
| 31 | 3.1 | 17.5 | 14.4 | 1.71 | 1.00 | 2.16 | 1.11 |
| 32 | 3.0 | 17.8 | 14.8 | 1.59 | 1.00 | 2.06 | 1.13 |
| 33 | 5.9 | 17.8 | 11.9 | 3.32 | 1.00 | 4.25 | 1.11 |

From the above table, it will be apparent to those skilled in the art that practice of the process of this invention makes it readily possible to separate p-xylene in the front end of an adsorption cycle. For example, in control Example 1–2, containing no pyridine, it will be apparent that since the selectivities of ethylbenzene and meta-xylene relative to p-xylene are less than 1.0, the former two will appear at the front end of the cycle and the p-xylene will appear at the middle of the cycle. The o-xylene is more strongly adsorbed than para-xylene and will appear at the end of the control cycle.

In experimental Examples 3–4, it will be apparent that, in the presence of pyridine modifier, the selectivities are substantially modified; each of the other three isomers is adsorbed more strongly than para-xylene so that para-xylene will appear at the front end of an adsorption cycle. Meta-xylene is most strongly adsorbed (selectivity 2.36 to 3.50) and will appear at the back end of the cycle. Ethylbenzene is somewhat less strongly adsorbed than meta-xylene (selectivity 1.87 to 2.47) and ortho-xylene is still less strongly adsorbed (selectivity 1.44–1.42). Selectivity of both meta-xylene and ethylbenzene increases with pyridine loading, but that of ortho-xylene does not change greatly. A similar pattern is observed in Examples 5 through 8 in which the zeolite powder used was from the same source as in Examples 1–4. Examples 9–18 were carried out using two different stocks of zeolite powder (without binder) both of which provided appreciably greater total capacity than the zeolite of Examples 1–8; it is considered probable that the zeolite used in Examples 1–8 contained occluded solids within the pore structure which restricted its capacity. Selectivity characteristics, including the effect of added pyridine, are similar for both the high and low capacity zeolites, although the extent of the selectivity increase for meta-xylene and ethylbenzene relative to para-xylene is smaller for the high capacity zeolites at a given pyridine loading level.

Examples 19–33 were carried out using zeolites containing binder material. Total capacities in these examples are lower than those of Examples 9–18 by an amount consistent with the presence of about 20% inert material. Selectivities, including the effect of added pyridine, follow the same pattern as those obtained with binder-free zeolites.

Figure 5:
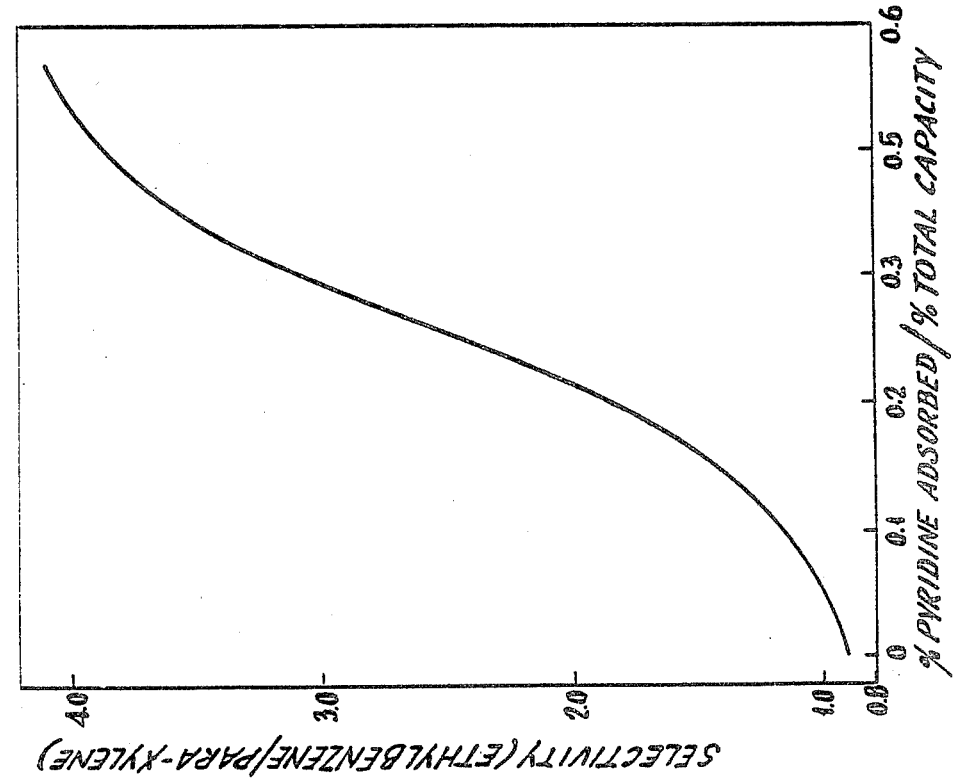
FIG. 5 presents an illustrative curve for pyridine-modified NaX zeolites showing Selectivity (of ethylbenzene/para-xylene) as a function of the ratio of % pyridine adsorbed/% total capacity.

When the values for selectivity of ethylbenzene relative to para-xylene from Examples 1–33, as well as those from some additional tests made under similar conditions, are plotted against pyridine loading expressed as a fraction (or percentage) of total adsorbent weight, a simple relationship is found for the various zeolite samples, high and low capacity, with and without binder, as shown in FIG. 5, where selectivity continuously increases with pyridine loading. A similar relationship for selectivity of meta-xylene relative to para-xylene is shown in FIG. 6. Selectivity of ortho-xylene relative to para-xylene remains roughly constant at a level below 1.5.

It is significant that the effect of pyridine modifier is essentially independent of factors (such as the presence of binder) affecting overall zeolite capacity and that the method of test is capable of detecting capacity variations and providing a basis for comparison of zeolite samples.

In the presence of the pyridine modifier, the selectivity relationships are seen to be drastically altered; and p-xylene is the least strongly adsorbed component in all cases in which pyridine is present.

Generally the order of increasing selectivity is unexpectedly changed from $M<EB<P<O$ in the absence of pyridine to $P<O<EB<M$ in the presence of pyridine.

As the pyridine loading is increased, selectivity for ethylbenzene and meta-xylene is seen to be increased while selectivity for o-xylene remains relatively unchanged.

It is also observed that C-8 capacity of the adsorbent is reduced by the amount of pyridine present. Optimum pyridine loading will depend upon a balance between the increase in selectivity and decrease in capacity with increasing pyridine loading.

EXAMPLES 34-46

In control Examples 34-46 there are presented equilibrium data obtained from tests with NaX zeolites using various modifiers (with approximate modifer loading as shown). The zeolites used in Examples 34-36 and 45-46 are from the same batch as those used in Examples 5-8; and those of Examples 37-44 are from the same batch as those used in Examples 1-4.

In Examples 37-38, the inert hydrocarbon was decalin (instead of the cyclohexane used in Examples 1-33).

In all other respects the same standard technique was used in Examples 34-46 as was used in Examples 1-33, except that the indicated modifier was employed instead of pyridine. The four C-8 components were present in the charge in equal proportions by weight.

The following Table presents the data in tabular form:

TABLE

| | Equilibrium Data - NaX Zeolites With Various Modifiers | | | | | | | |
|---|---|---|---|---|---|---|---|---|
| | | | Capacity | | | Selectivity | | |
| Example | Modifier | Modifier Loading | Total | C8 | EB | P | M | O |
| 34 | Water | 4 | — | 8.4 | 0.92 | 1.00 | 1.01 | 1.09 |
| 35 | Water | 8 | — | 7.0 | 1.00 | 1.00 | 0.94 | 1.09 |
| 36 | Water | 12 | — | 3.9 | 0.92 | 1.00 | 0.79 | 1.13 |
| 37 | Iso-propanol | 3 | 12.0 | 11.3 | 0.95 | 1.00 | 0.85 | 1.10 |
| 38 | Iso-propanol | 6 | 11.1 | 5.5 | 1.05 | 1.00 | 0.83 | 0.87 |
| 39 | Cyclo-hexanol | 3 | 12.0 | 9.4 | 0.84 | 1.00 | 0.94 | 1.12 |
| 40 | Cyclo-hexanol | 6 | 12.3 | 6.6 | 0.68 | 1.00 | 1.03 | 0.89 |
| 41 | t-butyl amine | 3 | 13.2 | 10.5 | 0.86 | 1.00 | 1.07 | 1.23 |
| 42 | t-butyl amine | 6 | 11.4 | 6.2 | 0.84 | 1.00 | 1.55 | 1.36 |
| 43 | n-butyl amine | 3 | 13.4 | 10.8 | 0.80 | 1.00 | 0.85 | 1.17 |
| 44 | n-butyl amine | 3 | 12.4 | 7.1 | 0.69 | 1.00 | 0.81 | 1.17 |
| 45 | Aniline | 2.9 | 11.8 | 9.0 | 0.87 | 1.00 | 0.95 | 1.38 |
| 46 | Aniline | 5.8 | 13.0 | 7.2 | 0.89 | 1.00 | 1.06 | 1.34 |

It will be apparent to those skilled in the art that none of the modifiers of control Examples 34-46 (which fall outside the scope of this invention) provides a significant, useful, selectivity effect, although some variations in selectivity (when measured against eg typical Examples 1-2 and 5-6 utilizing unmodified zeolite) are obtained.

By way of illustration, in control Example 34 ethylbenzene (selectivity of 0.92) would be the front-end product; the para- and meta-isomers (with almost identical selectivity of 1.00 and 1.01) would come out almost simultaneously and the ortho-isomer (selectivity 1.08) would come out only slightly after the para-isomer. In fact the selectivities are so close that the separation is de minimis in this control example. Compare this with eg Example 3 (carried out in accordance with this invention) wherein the para-isomer is the front end product and the next isomer (ortho-) which comes out has a selectivity (1.44) which is 44% greater than that of the para-isomer. Comparable observations may be made for Examples 34-46.

EXAMPLES 47-52

In these examples, data showing the effect of various pyridines on the C-8 aromatic selectivity properties of NaX zeolite are presented. The same batch of zeolite powder (containing no binder), activated at 800° F., was used in each of these examples. The same standard technique was used in Examples 47-52 as was used in Examples 1-33 except for the indicated change in the modifier employed; the four C-8 aromatics were present in the charge in equal proportions by weight. It is seen that pyridine se and the methyl pyridines change the NaX zeolite selectivity in the desired direction so that para-xylene is the least strongly adsorbed C-8 aromatic isomer. The quinolines do not provide this selectivity.

TABLE

| | Equilibrium Data - NaX Zeolites With Various Pyridine Modifiers | | | | | | | |
|---|---|---|---|---|---|---|---|---|
| | | Modifier | Capacity | | | Selectivity | | |
| Example | Modifier | Loading | Total | C8 | EB | P | M | O |
| 47 | None | — | 21.8 | 21.8 | 0.90 | 1.00 | 0.81 | 1.32 |
| 48 | Pyridine | 5.2 | 22.9 | 17.7 | 1.75 | 1.00 | 2.09 | 1.35 |
| 49 | 2-Picoline | 5.2 | 23.7 | 18.5 | 1.29 | 1.00 | 1.38 | 1.61 |
| 50 | 4-Picoline | 5.1 | 21.6 | 16.4 | 1.19 | 1.00 | 1.15 | 1.20 |
| 51 | Quinoline | 5.3 | 24.2 | 19.0 | 0.63 | 1.00 | 0.61 | 1.28 |
| 52 | Iso-quinoline | 5.0 | 23.1 | 18.0 | 0.81 | 1.00 | 0.75 | 1.26 |

EXAMPLES 53-62

This series of Examples presents data showing effect of the composition of C-8 aromatic components in the equilibrium liquid during adsorption on pyridine-modified NaX zeolite. The NaX zeolites in Examples 53-58 are from the same batches as the NaX zeolites used in Examples 1-8. The NaX zeolite in Examples 59-62 is from the same batch used in Examples 9-13. In each of these Examples, equilibrium data were obtained by the same standard procedure used in Examples 1-33. The ratio of C-8 aromatic isomers in the charge was varied. The weight ratio of isomers was as follows:

| Example | EB | P | M | O |
|---|---|---|---|---|
| 53 | 2 | 1 | 2 | 2 |
| 54 | 1 | 1 | 1 | 1 |
| 55 | 1 | 3 | 1 | 1 |
| 56 | 2 | 1 | 2 | 2 |
| 57 | 1 | 1 | 1 | 1 |
| 58 | 1 | 3 | 1 | 1 |
| 59 | 3 | 1 | — | — |
| 60 | 1 | 3 | — | — |
| 61 | — | 1 | 3 | — |
| 62 | — | 3 | 1 | — |

Equilibrium liquid compositions are in weight percent, reported on an inert-free basis.

In the binary ethylbenzene-para-xylene and meta-xylene—para-xylene mixtures of Examples 59-62, the change of Selectivity with concentration is also evident.

This fact is particularly important when para-xylene is recovered as a front-end product. It indicates that as separation of para-xylene progresses, further separation of this isomer becomes increasingly easy. Furthermore, if the ortho-isomer is separated at least in part by distillation prior to adsorption, the increased concentration of the para-isomer will make recovery of para-xylene easier. Still further improvement is effected if ethylbenzene is removed.

EXAMPLES 63-70

This series of Examples presents data showing the Selectivity as a function of the nature of the desorbent. Different desorbents are used in the eight Examples. In Example 68, the weight ratio of desorbent to C-8 hydrocarbons in the charge was 1:2. In each of the other Examples, the corresponding ratio was 1:1. The charge contained equal proportions, by weight, of each of the C-8 aromatics. The equilibrium test procedure was that described for Examples 1-33.

In Examples 63-65 and 68-70, the NaX zeolite was the same as that used in Examples 5-8. The zeolite in Examples 66 and 67 was the same as that used in Examples 19-23.

TABLE
EQUILIBRIUM DATA - PYRIDINE MODIFIED NaX ZEOLITE
EVALUATION OF DESORBENTS

| Example | Pyridine Loading | Desorbent | Capacity Total | C-8 + Desorbent | Selectivity EB | P | M | O | Desorb |
|---|---|---|---|---|---|---|---|---|---|
| 63 | 2.8 | Benzene | 12.6 | 9.8 | 1.20 | 1.00 | 2.32 | 1.60 | 2.60 |
| 64 | 2.8 | Toluene | 12.5 | 9.7 | 1.62 | 1.00 | 2.27 | 1.39 | 1.33 |
| 65 | 5.5 | Toluene | 12.8 | 7.3 | 2.20 | 1.00 | 3.64 | 1.48 | 2.16 |
| 66 | 2.9 | Toluene | 16.8 | 13.9 | 1.54 | 1.00 | 1.90 | 1.07 | 1.31 |
| 67 | 5.2 | Toluene | 15.0 | 9.8 | 3.15 | 1.00 | 4.10 | 1.25 | 2.57 |
| 68 | 2.9 | Naphthalene | 11.6 | 8.7 | 3.00 | 1.00 | 5.60 | 1.68 | 32.8 |
| 69 | 2.8 | 1,3-diethylbenzene | 11.0 | 8.2 | 1.75 | 1.00 | 1.73 | 1.29 | 0.57 |
| 70 | 2.8 | 1-methyl naphthalene | 10.5 | 7.7 | 4.14 | 1.00 | 4.99 | 0.96 | 10.3 |

TABLE
EQUILIBRIUM DATA - PYRIDINE MODIFIER NaX ZEOLITE
PARA-XYLENE SELECTIVITY AS A FUNCTION OF
COMPOSITION OF C-8 AROMATIC CHARGE

| Example | Pyridine Loading | Capacity Total | C-8 | Equilibrium Liquid Composition EB | P | M | O | Selectivity EB | P | M | O |
|---|---|---|---|---|---|---|---|---|---|---|---|
| 53 | 2.5 | 12.0 | 9.4 | 28.5 | 15.0 | 27.6 | 28.9 | 1.69 | 1.00 | 2.00 | 1.32 |
| 54 | 2.8 | 11.7 | 8.9 | 24.5 | 26.3 | 23.6 | 25.6 | 1.88 | 1.00 | 2.43 | 1.40 |
| 55 | 3.0 | 12.6 | 9.5 | 16.2 | 51.7 | 15.4 | 16.7 | 2.20 | 1.00 | 2.89 | 1.78 |
| 56 | 6.0 | 13.2 | 7.2 | 28.5 | 15.2 | 26.8 | 29.5 | 2.31 | 1.00 | 3.57 | 1.29 |
| 57 | 5.4 | 11.4 | 6.0 | 24.4 | 26.4 | 23.2 | 26.0 | 3.44 | 1.00 | 5.34 | 1.59 |
| 58 | 5.7 | 12.0 | 6.2 | 16.3 | 51.2 | 15.3 | 17.2 | 2.81 | 1.00 | 4.39 | 1.48 |
| 59 | 5.8 | 23.8 | 18.1 | 72.2 | 27.8 | — | — | 2.02 | 1.00 | — | — |
| 60 | 5.6 | 23.5 | 17.9 | 20.0 | 80.0 | — | — | 2.81 | 1.00 | — | — |
| 61 | 5.7 | 22.8 | 17.1 | — | 28.5 | 71.5 | — | — | 1.00 | 2.62 | — |
| 62 | 5.4 | 23.3 | 17.9 | — | 81.0 | 19.0 | — | — | 1.00 | 3.92 | — |

With the exception of Example 57, which is the same as Example 8, (the results of which appear unexpectedly to be out of line with the mass of data presented in Examples 1-33), there is an increase in Selectivity for ethylbenzene and meta-xylene relative to para-xylene as the concentration of para-xylene increases (at a given pyridine loading) in the four component C-8 aromatic mixtures.

From the Table, it appears for example that toluene is a suitable desorbent since it desirably has little effect on C-8 Selectivity and its relative adsorption strength is between those of para-xylene and ethylbenzene. Note that the C-8 aromatic Selectivities in Examples 64-67, using toluene as desorbent, compare favorably with those of Examples 7-8 and 22-23 which have comparable pyridine loading on comparable NaX zeolites, but are desorbent-free. Toluene is a desirable desorbent from the commercial point of view in that it is readily available and it has properties (e.g. boiling point) which make it desirable to use. Benzene is also shown to be a suitable desorbent; benzene selectivity relative to para-xylene is higher than any of the C-8 aromatic components. The ethylbenzene selectivity is undesirably lower (1.20) than is preferred.

Naphthalene and 1,3-diethylbenzene might be used; however naphthalene (selectivity of 32.8) is too strongly adsorbed and 1,3-diethylbenzene (selectivity 0.57) is too weakly adsorbed relative to the C-8 aromatic components. Thus they are less preferred desorbents.

1-Methylnaphthalene enhances ethylbenzene selectivity (4.14) and meta-xylene selectivity (4.99) but reduces ortho-xylene selectivity to less than 1.0. It is adsorbed much more strongly than the C-8 aromatics. This desorbent could be used in liquid phase operation if a final fractionation to remove ortho-xylene from the para-xylene were provided.

EXAMPLES 71-74

This series of examples presents data showing C-8 aromatic selectivity over a NaX zeolite having a Si:Al atom ratio of 1.44 and a lattice constant, obtained by X-ray diffraction, of 24.91. The equilibrium test procedure was that described for Examples 1-33 using a charge containing equal proportions by weight of each of the C-8 aromatics.

When the data in the Table are compared to the curves of FIGS. 5 and 6 it is seen that the ethylbenzene/para-xylene and meta-xylene/pyridine selectivities obtained with the high ratio (of Si to Al) X zeolite are higher than those with standard zeolite at the same pyridine loading.

TABLE
EQUILIBRIUM DATA - PYRIDINE MODIFIED
High Si:Al NaX Zeolite

| Example | Pyridine Loading W % of Absorbent | Pyridine Loading % of Total Cpy. | Capcity Total | Capcity C-8 Aromatics | Selectivity EB | Selectivity P | Selectivity M | Selectivity O |
|---|---|---|---|---|---|---|---|---|
| 71 | None | — | 22.9 | 22.9 | 0.90 | 1.00 | 0.89 | 1.31 |
| 72 | 2.7 | 12.9 | 21.6 | 18.9 | 1.33 | 1.00 | 1.45 | 1.25 |
| 73 | 5.5 | 24.0 | 22.9 | 17.4 | 2.77 | 1.00 | 3.20 | 1.73 |
| 74 | 7.8 | 34.7 | 22.5 | 14.7 | 4.23 | 1.00 | 4.97 | 1.78 |

EXAMPLES 75-77

The 50-200 mesh Linde NaX zeolite used in these runs is dried at 800° F., slurried with dry toluene in a dry box, and then loaded with 6 w % pyridine, basis dry zeolite, by addition of pyridine (in toluene solution). The system is allowed to equilibrate; and the NaX zeolite, loaded with 6 w % pyridine, is introduced into a glass column (5 feet long and 8 mm i.d.).

There is added to the column toluene desorbent in amount sufficient to totally submerge the pyridine-loaded NaX zeolite bed.

The run proper is started by addition of 10 ml of C-8 aromatic charge (of composition noted in the table which follows) at a rate of about 1 ml per minute; and after the aromatic charge, an excess of toluene desorbent is put through the column at the same flow rate. Temperature of operation is ambient —ca 75° F.—liquid phase operation.

The effluent is recovered in small individual cuts using a fraction collector; these cuts are analyzed by gas chromatography. The run for each Example is considered ended when the effluent shows toluene concentrations approaching 100%. In practice, this occurs after about 40 different individual cuts have been collected for a run. The column is flushed with excess toluene between Examples.

Representative analytical samples taken near the front and back ends of the cycles of each Example, are shown in the Table which follows. The NaX zeolite used is the same as that used in Examples 19-23. The Table shows, for each of Examples 75-77 the weight ratio of component, in the charge and in the noted cut. Weight ratios are expressed with respect to para-xylene.

TABLE

| | | Weight Ratio EB | Weight Ratio P | Weight Ratio M | Weight Ratio O |
|---|---|---|---|---|---|
| Example 75 | | | | | |
| Charge | | 1.004 | 1.00 | 2.010 | 1.011 |
| Cut 13 | Front | 0.652 | 1.00 | 0.784 | 1.012 |
| Cut 14 | End | 0.686 | 1.00 | 0.976 | 1.063 |
| Cut 27 | Back End | 1.618 | 1.00 | 3.742 | 0.839 |
| Example 76 | | | | | |
| Charge | | 0.037 | 1.00 | 0.037 | 0.038 |
| Cut 15 | Front | 0.019 | 1.00 | 0.010 | 0.032 |
| Cut 16 | End | 0.019 | 1.00 | 0.013 | 0.035 |
| Cut 26 | Back End | 0.062 | 1.00 | 0.075 | 0.037 |
| Example 77 | | | | | |
| Charge | | 0.032 | 1.00 | 0.033 | — |
| Cut 12 | Front | 0.016 | 1.00 | 0.006 | — |
| Cut 13 | End | 0.016 | 1.00 | 0.010 | — |
| Cut 26 | Back End | 0.067 | 1.00 | 0.083 | — |

It is apparent that these data indicate that para-xylene is less strongly adsorbed and that it is possible to obtain a front-end cut which is enriched in para-xylene with respect to ethylbenzene and meta-xylene, although separation from ortho-xylene is poor. In the case of Example 75, while the charge contains about equal parts of para-xylene and ethylbenzene, the front end cuts contain only about 65-68% as much ethylbenzene as para-xylene. The meta-content of the front end is down to about 40% of that originally present. Separation between para- and ortho-isomers is poor. These results are in general agreement with the selectivities set forth in the Tables for Examples 1-33 and Examples 53-62.

EXAMPLES 78-80

In these Examples, adsorption runs are made in the cyclic mode using a column constructed of ⅜ inch OD during having a 0.035 inch wall. The column, 15 feet long, is charged with 50-150 mesh NaX zeolite which has been pretreated in the same manner as the zeolite used in Example 75-77, and similarly loaded with Pyridine (6 w %) prior to being placed in the column.

Charge stock is a nominal 1:1:2 ratio (weight basis) ethylbenzene:para-xylene:meta-xylene mixture which contains about 1% ortho-xylene in the final blend. This corresponds to a typical refinery stream obtained from catalytic reforming followed by distillation to remove most of the ortho-xylene. Toluene is used as desorbent after passage through an in-line drier. Charge volume is 10 ml. in each cycle and flow rate is 1 ml per minute for both charge and desorbent. Excess toluene desorbent is passed through the column between cycles and also during the period in which operating temperature is being established.

The temperatures of operation (all in liquid phase) are:

| Example | Temperature |
|---------|-------------|
| 78 | Ambient (ca 75° F.) |
| 79 | 215° F. |
| 80 | 340° F. |

The results are plotted in FIG. 1 which shows the purity of the front-end p-xylene cut (desorbent-free basis) as a function of p-xylene yield (percentage of p-xylene in the charge which is recovered in the front-end cut). It will be noted that a typical point on the ambient temperature curve, eg the point having the coordinates (18, 40), indicates that 18 w % of the para-xylene charged is recovered in purity of 40 w % at ambient temperature. In the case of 215° F. operation, the curve shows e.g. that 10 w % of the para-xylene charged is recovered in purity of e.g. 90 w %.

It is apparent from inspection of the liquid phase curves plotted in FIG. 1, that separation efficiency (i.e. ability to attain high purity para-xylene) is increased by operation at elevated temperatures. Clearly the separation efficiency increases substantially as temperature is raised from ambient up to 215° F., but little or no change is observed in this liquid-phase embodiment as the temperature is increased further to 340° F.

EXAMPLE 81

The procedure of Examples 78-80 is duplicated except that separation is carried out at 340° F. in vapor phase at atmospheric discharge pressure. Nominal charge volume is 10 ml and nominal flow rate is 0.5 ml per minute, as measured in the liquid phase at ambient temperature.

Results are included in FIG. 1. Over 19.4 w % of the p-xylene charged is recovered in purity approaching 100%. Over 45 w % of the para-xylene charged is recovered in 99 w % purity and about 90 w % of the para-xylene charged can be recovered in 90 w % purity.

From FIG. 1, it is clear that vapor phase operation at 340° F. produces substantially greater separation efficiency than does liquid phase operation at the same or at a lower temperature.

EXAMPLE 82

In this Example, a series of cycles is carried out in which the conditions of Example 81 are duplicated except that pyridine is added to the toluene desorbent (prior to admission of the adsorption column) in amounts corresponding to about 0.17 w % to 0.28 w % based on toluene. This amount of pyridine is intended to compensate for pyridine losses during operation. The toluene-pyridine is dried prior to use by contact with solid sodium hydroxide. Flow rates up to one ml/min (measured in liquid phase at ambient temperature) are used in these cycles.

It is found that up to 53.0 w % of the para-xylene charged is recovered in purity approaching 100 w %.

EXAMPLE 83

In this Example, the conditions of Example 82 are duplicated except that the total volume of charge material in each cycle is 6 ml (rather than 10 ml as in Example 82) and the flow rates are all one ml/min.

It is found that up to 63.6 w % of the para-xylene charged is recovered in purity approaching 100 w %.

EXAMPLE 84

There are presented in FIG. 2 effluent concentration curves for a four-component mixture which may be typical of those of present commercial interest. Charge contains Ethylbenzene (EB)—24.8 w %
Para-xylene (p-x)—25.2 w %
Meta-xylene (m-x)—48.7 w %
Ortho-xylene (O-x)—1.3 w %

A run is made in vapor phase at 340° F. in a 15 foot-×⅜inch O.d. column loaded with NaX zeolite which had been loaded with 6 w % pyridine. (Pyridine content in the vapor phase at this level may typically be ca 0.2 w %). Toluene desorbent containing 0.23 w % pyridine is used.

In a run, the column is purged with desorbent; flow of desorbent is interrupted and the charge (6.4 ml) is introduced and desorbent flow is continued until all C-8 is eluted from the column. The flow rate for both desorbent and charge is one ml/min measured in liquid phase at ambient temperature.

The results are plotted in FIG. 2 which shows the concentration (w %) in the effluent of each of the four components as a function of the effluent quantity in grams. Effluent concentrations are plotted on a logarithmic scale to bring out behavior in the low concentration regions. Curves for the individual components are indicated on the figures; the dashed lines represent the overall C-8 concentration envelope for regions where it does not coincide with individual component curves. The area above the overall C-8 envelope represents desorbent.

To fit the plot into available format without losing desired data, abscissas representing quantity of effluent use an expanded scale in the region where component separation occurs and a compressed scale at the end of the cycle where the most strongly adsorbed component tails out.

It will be apparent from this illustrative figure that it is possible to attain substantially pure para-xylene (free of other C-8 isomers) in high concentration relative to the desorbent, at the front end of the cycle. It is also of interest to note that a meta-xylene product, free of other C-8 isomers, is produced at the tail-end of the cycle (in the region of 21-34 grams of effluent).

EXAMPLE 85

In this Example, there is set forth one preferred embodiment indicating how the instant process may be carried out in commercial operation. FIG. 3 sets forth in schematic form a flow diagram of one preferred embodiment.

In this embodiment, the charge C-8 stream from which it is desired to recover para-xylene contains
ethylbenzene—20.0 w %
para-xylene—20.3 w %
meta-xylene—39.7 w %
ortho-xylene—20.0 w %

This stream is admitted through line 10 to distillation operation 11 wherein there is separated pure ortho-xylene, recovered through line 12.

The composition in line 13 typically may contain
ethylbenzene—24.7 w %
para-xylene—25.0 w %
meta-xylene—49.0 w %
ortho-xylene—1.3 w %

Adsorption operation 14 utilizes a 15 ft. long column containing 1000 parts of 50–120 mesh NaX zeolite which has been loaded with 60 parts of pyridine. The outlet of the column is at atmospheric pressure. Toluene desorbent containing 0.23 w % of pyridine, is admitted in the vapor phase at 340° F. through line 15 to the top of the column and passed through the adsorption bed at a flow rate such that the quantity of toluene introduced per unit time per unit cross section of adsorbent column is equivalent to 0.5 gallons of liquid toluene (measured at room temperature) per minute per square foot of column cross section.

Periodically, the flow of toluene vapor (in this example, all references to toluene from line 15 refer to toluene containing 0.23 w % pyridine) to the column from line 15 is interrupted and charge, in the vapor phase at 340° F., is admitted through line 13 to the top of the column and is passed through the adsorption bed at a flow rate such that the quantity of charge introduced per unit time per unit cross section of adsorbent column is equivalent to 0.5 gallons of liquid charge (measured at room temperature) per minute per square foot of column cross section. The flow of charge is continued until 43.8 parts of charge have been introduced. At this point, the flow of charge from line 13 is interrupted and the flow of toluene from line 15 is resumed.

Alternate introduction of charge and toluene desorbent is continued, the interval between sequential introductions of charge (or of toluene) comprising a single cycle. The quantity of toluene introduced during each cycle in this example is 188.2 parts. Time for a complete cycle is about 34.5 minutes. A larger quantity of toluene per cycle may be used without affecting product quality, but at the expense of greater cycle time and greater cost for separating desorbent from C-8 aromatic components. Use of a smaller quantity of toluene per cycle reduces the yield of pure product.

Effluent from the bottom of the column has a composition profile similar to that shown in FIG. 2, where a single complete cycle is considered here to comprise the effluent from the point where total C-8 aromatic content rises above 0.1 wt. % to the point where it falls below 0.1 wt. %. In each cycle, a first cut is taken through line 16 starting at the point where C-8 aromatic concentration reaches 0.1% and extending over a period of about 2.9 minutes. This first cut contains 6.4 parts off para-xylene to the exclusion (less than 1.0 wt. % of the para-xylene) of other C-8 isomers, plus 13.1 parts of toluene with about 0.23% pyridine, based on toluene. This mixture is separated by distillation in distillation operation 17 to permit recovery in line 18 of toluene and pyridine which may be recycled to line 15 with or without intermediate separation or purification. There is recovered in line 19, 6.4 parts of 99+ wt. % para-xylene.

The second cut, recovered in line 20, over a time period of about 2.8 minutes, contains 8.6 parts of C-8 isomers of which 71.8 w % is para-xylene, together with 10.3 parts of toluene containing 0.23% pyridine (based on toluene). This mixture is separated in distillation operation 21 to permit recovery in line 22 of toluene and pyridine which may be handled in manner similar to that for the comparable stream in line 18. The stream in line 23 (8.6 parts) is a para-xylene stream containing 71.8 w % para-xylene together with other C-8 isomers. This latter cut may be recycled, as to line 10. In the simplest mode of operation, it may be desirable to not separately recover this second cut, but to combine it with the third cut infra.

The third cut recovered in line 24, over a time period of about 14.4 minutes, contains little or no para-xylene in this embodiment. Typically it contains 25.2 parts of C-8 components of which less than 0.6% is para-xylene, and 71.5 parts of toluene with about 0.23% pyridine (based on toluene). This mixture is separated by distillation in distillation operation 25 to yield in line 26, 71.5 parts of toluene containing 0.23% pyridine, this stream being handled in manner similar to streams 18 and 22, either separately or in combination therewith. There may be recovered in line 27 a C-8 stream containing in this embodiment 0.55% of para-xylene, 28.0% of ethylbenzene, 0.7% of ortho-xylene, and 70.75% of meta-xylene.

In one embodiment, there is recovered a fourth cut through line 28 over a time period of about 14.4 minutes. This cut contains 93.3 parts of toluene with about 0.23% pyridine (based on toluene) and 3.6 parts of C-8 components including mainly meta-xylene. This mixture is separated in distillation operation 29 to yield in line 30, 93.3 parts of toluene containing 0.23% pyridine, this stream being handled in manner similar to streams 18, 22, and 30. There is recovered in line 31, 3.6 parts of meta-xylene of purity of 98.5w %. Alternatively, the third cut may be extended to the end of the cycle and the fourth cut omitted.

It will be apparent to those skilled in the art that this processing scheme may be modified depending on the concentration of the several components in the charge or upon the needs of the processor. For example, if only the para-xylene is desired, it may be desirable to recover the second, third, and fourth cuts together rather than separately. In another embodiment, it may be desirable to recover the third and fourth cuts together. The toluene-pyridine streams may be combined and recycled directly to line 15 or they may be fractionated to permit recovery of the separate components. The para-xylene stream recovered by distillation of the second cut may be recycled to charge in line 10 or passed to a separate separation system, etc.

EXAMPLE 86

In a more preferred embodiment of the process, the distillation operation 11 in FIG. 3 includes provision for removing ethylbenzene as well as ortho-xylene from a charge C-8 stream to produce a para-xylene/meta-xylene concentrate. When this is done, the composition in line 13 may be:
ethylbenzene—2.8 wt. %
para-xylene—29.6 wt. %
meta-xylene—65.7 wt. %
ortho-xylene—1.9 wt. %

Adsorption operation 14 utilizes the same 15 ft. long column used in Example 85. The column contains 1000 parts of 50–120 mesh NaX zeolite which has been loaded with 60 parts of pyridine and discharges to atmospheric pressure. Toluene desorbent containing 0.17 w % pyridine, in the vapor phase at 340° F. is admitted through line 15 to the top of the column and passed through the adsorption bed at a flow rate such that the quantity of toluene introduced per unit time per unit cross section of adsorption column is equivalent to 0.5 gallon of liquid toluene (measured at room temperature) per minute per square foot of column cross section.

Periodically, the flow of toluene (in this example, all references to toluene from line 15 refer to toluene containing 0.17 w % pyridine) to the column from line 15 is interrupted and charge, in the vapor phase at 340° F., is admitted through line 13 to the top of the column and is passed through the adsorption bed at flow rate equivalent to 0.5 gallon of liquid charge (measured at room temperature) per minute per square foot of column cross section. The flow of charge is continued until 69.4 parts of charge have been introduced. At this point, the flow of charge from line 13 is interrupted and the flow of toluene from line 15 is resumed. Alternate introduction of charge and toluene desorbent is continued, the interval between sequential introduction of charge (or of toluene) comprising a single cycle. The quantity of toluene introduced during each cycle is 215.8 parts and the time for a complete cycle is about 42.4 minutes.

In each cycle, a first cut of effluent is taken through line 16 starting at the point where C-8 aromatic concentration reaches 0.1% and extending over a period of about 3.9 minutes. This first cut contains 11.7 parts of para-xylene to the exclusion (less than 1.0 w % of the para-xylene) of other C-8 isomers plus 14.5 parts of toluene with about 0.17% pyridine, based on toluene. This mixture is separated by distillation in distillation operation 17 to permit recovery of toluene and pyridine for recycle and 11.7 parts of 99+ Wt. % para-xylene.

A second cut, recovered in line 20 over a time period of about 4.1 minutes contains 19.7 parts of C-8 isomers, of which about 41.9% is p-xylene, together with 7.9 parts of toluene with about 0.17% pyridine, based on toluene. The toluene and pyridine are separated from C-8 isomers in distillation operation 21 and are recovered in line 22 for recycle. The p-xylene-rich C-8 stream in line 23 (19.7 parts) may be recycled, as to line 10. In the simplest mode of operation, it may be desirable to not separately recover this second cut, but to combine it with the third cut infra.

A third cut, recovered in line 24 over a time period of about 13.0 minutes contains little p-xylene in this embodiment. Typically it contains 30.6 parts of C-8 components, of which less than 2% is p-xylene and 57.9 parts of toluene with about 0.17% pyridine based on toluene. This mixture is separated in distillation operation 25 to yield in line 26, 57.9 parts of toluene containing 0.17% pyridine this stream being handled in manner similar to streams 18 and 22, either separately or in combination therewith. There may be recovered in line 27 a C-8 stream containing predominantly meta-xylene with small amounts of ethylbenzene and ortho-xylene and about 1.5% para-xylene.

A fourth cut, recovered in line 28 over a time period of about 21.4 minutes contains 135.4 parts of toluene with about 0.17% pyridine, based on toluene, and 7.4 parts of C-8 components consisting mainly of meta-xylene. This mixture is separated in distillation operation 29 to recover in line 30 toluene and pyridine for recycle as well as, in line 31, 7.4 parts of meta-xylene of purity greater than 99 Wt. %. Alternately, the fourth cut may be subdivided into two cuts before distillation: the first contains the bulk of the high purity meta-xylene at a concentration of 8.9% in admixture with toluene; the second contains over 99% toluene with about 0.17% pyridine plus a small amount of C-8 isomers from the tail of the cycle.

EXAMPLES 87–90

This series of Examples is designed to show equilibrium behavior utilizing pyridine-modified LiX-type zeolites and also to determine comparable characteristics of alkali metal-type X zeolites in the presence of pyridine. The lithium X zeolite is prepared from the same lot of sodium X zeolite as was used in Examples 1–8 by exchange with an aqueous lithium acetate solution. 72.3 atom % of the sodium is found to be replaced with lithium. The zeolite is activated at 800° F. before use.

The potassium X zeolite is prepared from a different lot of NaX zeolite by exchange with aqueous KCl solution; 93.7 atom % of the sodium is found to be replaced with potassium. This zeolite is activated at 800° F. before use.

The procedure followed is as set forth in connection with Examples 1–33 using a charge containing equal proportions, by weight, of each of the C-8 aromatics. There are tabulated infra data showing the results for lithium X-zeolite and for potassium X zeolite. Examples 7–8 for sodium X are included for comparison.

TABLE

| Example | Cation | Pyridine Loading | Capacity Total | Capacity C-8 | Selectivity EB | Selectivity P | Selectivity M | Selectivity O |
|---|---|---|---|---|---|---|---|---|
| 87 | Li | 2.9 | 19.9 | 17.0 | 1.56 | 1.00 | 1.95 | 1.66 |
| 88 | Li | 5.4 | 17.3 | 11.9 | 2.64 | 1.00 | 3.13 | 1.87 |
| 89 | K | 3.2 | 18.6 | 15.4 | 1.18 | 1.00 | 0.37 | 0.44 |
| 90 | K | 5.9 | 19.6 | 13.7 | 1.17 | 1.00 | 0.43 | 0.46 |
| 7 | Na | 2.8 | 11.7 | 8.9 | 1.88 | 1.00 | 2.43 | 1.40 |
| 8 | Na | 5.4 | 11.4 | 6.0 | 3.44 | 1.00 | 5.34 | 1.59 |

Equilibrium Data (Liquid Phase 75° F.) on Alkali X Type Zeolites

From the table, it is apparent that in the case of LiX zeolite (as with NaX-type zeolite) para-xylene is the least strongly adsorbed C-8 aromatic isomer and thus will be produced as a front-end product. Generally it may be noted that performance of these two zeolites (with respect to front-end separation of para-xylene) is comparable.

It will also be apparent that use of a comparable potassium X-type zeolite, gives results which are totally different. In that instance, the front-end product is meta-xylene and the presence of pyridine does not greatly change the selectively characteristics of the original adsorbent (without pyridine).

EXAMPLES 91–104

In this series of Examples, equilibrium data are obtained in liquid phase at 75° F. in manner comparable to that of Examples 1–33 using a charge containing equal proportions by weight of each of the C-8 aromatics. Examples 91–99 are carried out using LiX zeolite with no binder while the zeolites of Examples 100–104 contained binder.

Comparison of experimental Examples 95-97 and 100-104 with control Examples 91-94 and 98-99 clearly reveals that only by use of pyridine modifier is the difference in selectivity such that it is readily possible to attain front-end separation of high purity para-xylene.

It is found that pyridine-modified LiX zeolite behavior is similar to that of pyridine-modified NaX zeolite with respect to selectivity for ethylbenzene and meta-xylene relative to para-xylene. When these selectivities (on LiX zeolite) are plotted against pyridine loading expressed as a fraction of total adsorbent capacity, as was done for NaX zeolite in FIGS. 5 and 6, it is found the LiX zeolite data fall close to the curves derived from NaX data. Selectivity of ortho-xylene relative to para-xylene remains fairly constant throughout the pyridine loading range and is appreciably higher than the ortho/para selectivity on NaX zeolite. Thus front end separation of para-xylene on pyridine-modified LiX zeolite is less affected by increased concentration of ortho-xylene in the feed than is separation on NaX zeolite.

zeolite was the same as that used in Examples 91-92 and 95-97.

From the table, it appears that benzene and toluene are suitable desorbents, having relatively little effect on adsorbent selectivity for the C-8 aromatic isomers and having relative adsorption strengths (as indicated by selectivities relative to para-xylene) near the middle of the C-8 aromatic range. Naphthalene and 1,3-diethylbenzene are of little interest, being too strongly and weakly adsorbed, respectively; 1-methylnaphthalene may be a suitable desorbent under certain circumstances.

TABLE

Equilibrium Data - Pyridine Modified LiX Zeolite
Evaluation of Desorbents

| Example | Pyridine Loading | Desorbent | Capacity Total | C-8 + Desorbent | Selectivity EB | P | M | O | Desorb. |
|---|---|---|---|---|---|---|---|---|---|
| 105 | 3.2 | Benzene | 20.9 | 17.7 | 1.40 | 1.00 | 2.27 | 2.09 | 1.87 |
| 106 | 3.0 | Toluene | 19.9 | 16.9 | 1.49 | 1.00 | 2.03 | 1.66 | 1.53 |
| 107 | 6.4 | Toluene | 19.6 | 13.2 | 2.50 | 1.00 | 3.57 | 1.86 | 2.20 |
| 108 | 3.1 | Naphthalene | 18.8 | 15.7 | 1.82 | 1.00 | 2.04 | 1.80 | 11.0 |
| 109 | 3.3 | 1-Methylnaphthalene | 17.4 | 14.2 | 2.06 | 1.00 | 2.08 | 1.16 | 3.70 |
| 110 | 3.3 | 1,3-Diethylbenzene | 18.7 | 15.4 | 1.10 | 1.00 | 1.32 | 1.47 | 0.66 |

TABLE

Equilibrium Data on LiX Zeolite
With and Without Modifier

| Example | Modifier | Modifier Loading | Capacity Total | C-8 | Selectivity E-B | P | M | O |
|---|---|---|---|---|---|---|---|---|
| 91 | None | | 20.8 | 20.8 | 1.10 | 1.00 | 1.26 | 1.87 |
| 92 | none | | 21.3 | 21.3 | 1.09 | 1.00 | 1.26 | 1.83 |
| 93 | None | | 20.1 | 20.1 | 1.14 | 1.00 | 1.28 | 1.90 |
| 94 | None | | 20.3 | 20.3 | 1.14 | 1.00 | 1.29 | 1.95 |
| 95 | pyridine | 2.8 | 19.4 | 16.6 | 1.49 | 1.00 | 1.83 | 1.61 |
| 96 | pyridine | 2.9 | 19.9 | 17.0 | 1.56 | 1.00 | 1.95 | 1.66 |
| 97 | pyridine | 5.4 | 17.3 | 11.9 | 2.64 | 1.00 | 3.13 | 1.87 |
| 98 | None | | 19.9 | 19.9 | 1.07 | 1.00 | 1.18 | 1.87 |
| 99 | None | | 19.6 | 19.6 | 1.07 | 1.00 | 1.19 | 1.86 |
| 100 | Pyridine | 2.7 | 19.6 | 16.8 | 1.62 | 1.00 | 2.01 | 1.82 |
| 101 | Pyridine | 2.7 | 19.6 | 16.9 | 1.59 | 1.00 | 1.98 | 1.82 |
| 102 | Pyridine | 5.4 | 20.0 | 14.5 | 2.54 | 1.00 | 3.32 | 1.94 |
| 103 | Pyridine | 5.6 | 20.1 | 14.5 | 2.63 | 1.00 | 3.48 | 1.93 |
| 104 | Pyridine | 5.6 | 19.6 | 14.0 | 2.83 | 1.00 | 3.77 | 1.99 |

EXAMPLES 105-110

This series of examples presents data showing C-8 aromatic selectivity (on pyridine-modified LiX zeolite) relative to para-xylene as a function of the nature of the desorbent, as well as selectivity of the desorbent relative to para-xylene. Different desorbents are used in these examples. In Example 108, the weight ratio of desorbent to total C-8 hydrocarbons in the charge was 1:2; in each of the other examples, the corresponding ratio was 1:1. The charge contained equal proportions, by weight, of each of the C-8 aromatics. The equilibrium test procedure was that described for examples 1-33. The LiX

EXAMPLES 111-116

In these examples, data showing the effect of various pyridines on the C-8 aromatic selectivity properties of LiX zeolite are presented. The same batch of zeolite (containing binder) was used in each of these examples. The equilibrium test procedure was the same as that described in Examples 1-33 using a charge containing equal proportions, by weight, of each of the C-8 aromatics. It is seen that pyridine se and the methylpyridines improve the selectivity of the adsorbent with respect to separation of para-xylene as a least strongly adsorbed component. The effect of quinolines is much smaller.

TABLE

Equilibrium Data - LiX Zeolite
With Various Pyridine Modifiers

| Example | Modifier | Modifier Loading | Capacity Total | C-8 | Selectivity EB | P | M | O |
|---|---|---|---|---|---|---|---|---|
| 111 | None | — | 19.9 | 19.9 | 1.07 | 1.00 | 1.18 | 1.87 |
| 112 | Pyridine | 5.6 | 19.6 | 14.0 | 2.83 | 1.00 | 3.77 | 1.99 |
| 113 | 2-Picoline | 5.6 | 20.4 | 14.8 | 1.66 | 1.00 | 2.37 | 2.07 |
| 114 | 4-Picoline | 5.6 | 19.9 | 14.4 | 1.65 | 1.00 | 2.26 | 2.20 |
| 115 | Quinoline | 5.5 | 20.0 | 14.5 | 1.11 | 1.00 | 1.32 | 2.06 |
| 116 | Isoquinoline | 5.6 | 20.1 | 14.5 | 1.19 | 1.00 | 1.36 | 2.14 |

EXAMPLE 117

A run, similar to that of Example 84, is made in vapor phase in a 15 foot × ⅜ inch o.d. column packed with 50-120 mesh LiX zeolite which had been loaded with 3 w % pyridine. (Pyridine content in the vapor phase at this level may typically be ca 0.004 wt. %) Toluene desorbent containing 0.0045 wt. % pyridine is used. The charge stock is a nominal 1:1:2 ratio (weight basis) enthylbenzene; para-xylene; meta-xylene mixture which contains about 1% ortho-xylene in the final blend.

In the run, the column is purged with desorbent; flow of desorbent is interrupted and the charge (10.2 ml) is introduced; then desorbent flow is continued until all C-8 is eluted from the column. The flow rate for both desorbent and charge is ½ ml/min measured in liquid phase at ambient temperature.

The results are plotted in FIG. 4 which shows results in the same manner described in Example 84 for FIG. 2. It will be apparent from this illustrative figure that it is possible to attain substantially pure para-xylene (free of other C-8 isomers), in high concentration relative to desorbent, at the front end of the cycle. It is also of interest to note that ortho-xylene is concentrated in a much later portion of the cycle here than in Example 84, FIG. 2, for NaX zeolite.

EXAMPLE 118

In this example, calculation of equilibrium properties from experimental equilibrium data using my test method is illustrated for a case corresponding to Example 23 using as adsorbent, a composite containing 80% NaX zeolite and 20% clay binder.

(i) there is added to the charge composition, containing ethylbenzene, p-xylene, m-xylene, o-xylene, and pyridine, a known weight of cyclohexane (inert component) and the resulting test liquid composition has the following composition:

| Component | Weight, g | Composition, Wt % | |
|---|---|---|---|
| | | Inert-free | Overall |
| cyclohexane | 1.09326 | — | 57.00 |
| ethylbenzene | 0.19103 | 23.16 | 9.960 |
| para-xylene | 0.19187 | 23.26 | 10.003 |
| meta-xylene | 0.19147 | 23.22 | 9.983 |
| ortho-xylene | 0.19264 | 23.36 | 10.044 |
| pyridine | 0.05769 | 7.00 | 3.088 |

(ii) the test procedure includes 14-day equilibration of 0.9810 g of dry adsorbent with 1.9180 g of test liquid composition.

(iii) Equilibrium liquid is sampled and analyzed; the mean of two GC analyses is:

| Component | Composition Wt. % | |
|---|---|---|
| | Inert-free | Overall |
| cyclohexane | — | 62.70 |
| ethylbenzene | 23.42 | 8.736 |
| para-xylene | 27.34 | 10.198 |
| meta-xylene | 23.28 | 8.310 |
| ortho-xylene | 26.97 | 10.060 |
| pyridine* | 0 | 0 |

*assumed to be completely adsorbed (iv) The quantity of cyclohexane (inert component which is not adsorbed) in the equilibrium liquid is the same as that in the charge (57.00%×1/100×1.9180 g charge=1.09326 g) and comprises 62.70% of the equilibrium liquid.

The remainder (37.30% of the equilibrium liquid contains C-8 aromatics.

The quantity of each C-8 aromatic component in the equilibrium liquid is calculated from the analysis and the weight of cyclohexane in the equilibrium liquid. The quantity of pyridine in the equilibrium liquid is negligible. The Table shows the weight (g) of components at equilibrium, calculated as follows:

TABLE $$\frac{\% \text{ Component (Equil)}}{\% \text{ Cyclohexane (Equil)}} \times \text{Wt. Cyclohexane g} = \frac{\text{Wt}}{\text{Component (Equil), g}}$$

| Component | Wt. Component (Equil), g |
|---|---|
| ethylbenzene | (8.736/62.70) × 1.09326 = 0.15232 g |
| para-xylene | (10.198/62.70) × 1.09326 = 0.17782 g |
| meta-xylene | (8.310/62.70) × 1.09326 = 0.14490 g |
| ortho-xylene | (10.060/62.70) × 1.09326 = 0.17541 g |

(v) The quantity of each component adsorbed per unit weight of adsorbent is the difference between the weight of component in the charge and equilibrium liquid, divided by the weight of adsorbent (0.9810 g) used in the test.

| Component | Wt. Component Adsorbed/Wt. Adsorbent |
|---|---|
| ethylbenzene | (0.19103 − 0.15232)/0.9810 = 0.03946 |
| para-xylene | (0.19187 − 0.17782)/0.9810 = 0.01432 |
| meta-xylene | (0.19147 − 0.14490)/0.9610 = 0.04747 |
| ortho-xylene | (0.19264 − 0.17541)/0.9810 = 0.01756 |
| pyridine | (0.05769 − 0)/0.9810 = 0.05881 |

Total capacity, of the adsorbent for C-8 aromatics plus pyridine is 0.1776 g/g adsorbent, or 17.76%(Wt.); of this, 0.0588 g/g adsorbent, or 5.88% (wt.), is the pyridine loading, and 0.1188 g/g adsorbent, or 11.88%(wt.), is the C-8 aromatic loading.

(vi) Composition of C-8 aromatics (pyridine-free basis) in the adsorbed phase is calculated from the adsorption weights.

| Component | Composition in Adsorbed Phase, % Wt. |
|---|---|
| ethylbenzene | (0.03946/0.1188)(100) = 33.22 |
| para-xylene | (0.01432/0.1188)(100) = 12.05 |
| meta-xylene | (0.04747/0.1188)(100) = 39.96 |
| ortho-xylene | (0.01756/0.1188)(100) = 14.78 |

(vii) Selectivity of the pyridine-modified adsorbent for each of the C-8 aromatics relative to para-xylene is calculated from the equilibrium liquid and adsorbed phase compositions:

$$\alpha \, A/B = \frac{\left(\frac{\text{conc. component A}}{\text{conc. component B}}\right) \text{Adsorbed phase}}{\left(\frac{\text{conc. component A}}{\text{conc. component B}}\right) \text{Equilibrium liquid}}$$

| Components (A/B) | Selectivity, α A/B |
|---|---|
| ethylbenzene/para-xylene | $\left(\frac{33.22}{12.05}\right) / \left(\frac{23.42}{27.34}\right) = 3.22$ |
| para-xylene/para-xylene | $\left(\frac{12.05}{12.05}\right) / \left(\frac{27.34}{27.34}\right) = 1.00$ |
| meta-xylene/para-xylene | $\left(\frac{39.96}{12.05}\right) / \left(\frac{22.28}{27.34}\right) = 4.07$ |
| ortho-xylene/para-xylene | $\left(\frac{14.78}{12.05}\right) / \left(\frac{26.97}{27.34}\right) = 1.24$ |

In summary of this method of determining, as properties of an adsorbent, (a) the selectivity for one component of a liquid charge composition, with respect to a reference component of said charge composition, and (b) the capacity for adsorbing the components from said liquid composition, the following steps are carried out:

(i) adding to said liquid charge composition a known weight of an essentially inert liquid component which is not appreciably adsorbed from the mixture by said adsorbent in the presence of said liquid charge composition thereby forming a test liquid composition;

(ii) equilibrating said test liquid composition in the presence of said adsorbent thereby forming an equilibrium liquid in the presence of said adsorbent;

(iii) determining the % concentration, in said equilibrium liquid, of said essentially inert liquid component, said reference component, and at least one other component, the selectivity for which is to be determined with respect to said reference component;

(iv) determining the weight in said equilibrium liquid of said reference component and said other component, from the concentration of each in the equilibrium liquid and the weight of essentially inert component present in the equilibrium liquid;

(v) determining the capacity weights of said reference component and said other component which are adsorbed per unit weight of adsorbent by the difference between the weights of said reference component and of said other component in the charge and in the equilibrium liquid divided by the weight of adsorbent;

(vi) determining the ratio between concentration of said reference component and said other component in the adsorbed phase; and (vii) determining the selectivity for said other component with respect to said reference component by dividing the ratio of the concentration of said other component in the adsorbed phase to the concentration of said reference component in the adsorbed phase by the ratio of the concentration of said other component in the equilibrium liquid to the concentration of said reference component in the equilibrium liquid.

It will be apparent that the capacity of an adsorbent for a particular component (the capacity weight) determined in step (v) may be expressed as weight of component per weight of adsorbent. Commonly it is expressed in terms of a percentage i.e. weight of component(s) per 100 weights of adsorbent. In illustrative Example 118, the total capacity (17.8) and the C-8 capacity (11.9) tabulated for Example 23 may be calculated as follows:

$$
\begin{array}{r}
0.03946 \\
0.01432 \\
0.04747 \\
\underline{0.01756} \\
0.11881
\end{array}
$$

$\frac{0.11881}{100} = 11.9\%$     C-8 Capacity.

Total Capacity
$$
\begin{array}{r}
0.11881 \\
\underline{0.05881} \\
0.17762
\end{array}
$$

$\frac{0.17762}{100} = 17.8\%$     Total Capacity

In summary of this method of determining, as properties of an adsorbent, (a) selectivity for m-xylene or o-xylene or ethylbenzene in a liquid charge C-8 composition (with respect to a p-xylene reference component of a charge composition) in the presence of an adsorbent, and (b) capacity for adsorbing the components of said liquid composition, the following steps are carried out:

(i) adding to said liquid charge composition a known weight of cyclohexane inert liquid component which is not appreciably adsorbed from the mixture by said adsorbent in the presence of said liquid charge composition thereby forming a test liquid composition;

(ii) equilibrating said test liquid composition in the presence of said adsorbent thereby forming an equilibrium liquid in the presence of said adsorbent;

(iii) determining the % concentration, in said equilibrium liquid, of said cyclohexane essentially inert liquid component, said p-xylene reference component, and at least one other of said m-xylene or o-xylene or ethylbenzene component, the selectivity for which is to be determined with respect to said p-xylene reference component;

(iv) determining the weight in said equilibrium liquid of said p-xylene reference component and said other component, from the concentration of each in the equilibrium liquid and the weight of cyclohexane essentially inert component present in the equilibrium liquid;

(v) determining the capacity weights of said p-xylene reference component and of said other component which are adsorbed per unit weight of adsorbent by the difference between the weights of said p-xylene reference component and of said other component in the charge and in the equilibrium liquid divided by the weight of adsorbent;

(vi) determining the ratio between the concentration of said p-xylene reference component and said other component in the adsorbed phase; and (vii) determining the selectivity for said other component with respect to said p-xylene reference component by dividing the ratio of the concentration of said other component in the adsorbed phase to the concentration of said p-xylene reference component in the adsorbed phase by the ratio of the concentration of said other component in the equilibrium liquid to the concentration of said p-xylene reference component in the equilibrium liquid.

Although this invention has been illustrated by reference to specific embodiments, it will be apparent to those skilled in the art that various changes and modifications may be made which clearly fall within the scope of this invention.

I claim:

1. The method of determining, as a property of an adsorbent, the selectivity for one component of a liquid charge composition with respect to a reference component of said charge composition with comprises (i) adding to said liquid charge composition a known weight of an essentially inert liquid component which is not appreciably adsorbed from the liquid charge composition by said adsorbent in the presence of said liquid charge composition thereby forming a test liquid composition;

(ii) equilibrating said test liquid composition at ambient temperature in the presence of said adsorbent thereby forming an equilibrium liquid in the presence of said adsorbent;

(iii) determining the % concentration, in said equilibrium liquid, of said essentially inert liquid component, said reference component, and at least one other component, the selectivity for which is to be determined with respect to said reference component;

(iv) determining the weight in said equilibrium liquid of said reference component and said other component, from the concentration of each in the equilibrium liquid and the weight of essentially inert component present in the equilibrium liquid;

(v) determining the capacity weights of said reference component and said other component which are adsorbed per unit weight of adsorbent by the difference between the weight of said reference component of said other component in the charge and in the equilibrium liquid divided by the weight of adsorbent;

(vi) determining the ratio between concentration of said reference component and of said other component which is adsorbed; and (vii) determining the selectivity of said component with respect to said reference component by dividing the ratio of the concentration of said other component which is adsorbed to the concentration of said reference component which is adsorbed by the ratio of concentration of said other component in the equilibrium liquid to the concentration of said reference component in the equilibrium liquid, said selectivity determined at ambient temperature being useful for separations at elevated temperature.

2. The method as claimed in claim 1 wherein the total capacity of said adsorbent is determined by adding the capacity weights of all components in the liquid charge composition.

3. The method of determining, as a property of an adsorbent, the selectivity of m-xylene or o-xylene or ethylbenzene in a liquid charge C-8 composition with respect to a p-xylene reference component of said charge composition which comprises (i) adding to said liquid charge composition a known weight of cyclohexane inert liquid component which is not appreciably adsorbed from the liquid charge C-8 composition by said adsorbent in the presence of said liquid charge composition thereby forming a test liquid composition;

(ii) equilibrating said test liquid composition at ambient temperature in the presence of said adsorbent thereby forming an equilibrium liquid in the presence of said adsorbent;

(iii) determining the % concentration, in said equilibrium liquid, of said cyclohexane essentially inert liquid component, said p-xylene reference component, and at least one other of said m-xylene or o-xylene or ethylbenzene components, the selectivity for which is to be determined with respect to said p-xylene reference component;

(iv) determining the weight in said equilibrium liquid of said p-xylene reference component and said other component, from the concentration of each in the equilibrium liquid and the weight of cyclohexane essentially inert component present in the equilibrium liquid;

(v) determining the capacity weights of said p-xylene reference component and of said other component which are adsorbed per unit weight of adsorbent by the difference between the weight of said p-xylene reference component and of said other component in the charge and in the equilibrium liquid divided by the weight of adsorbent;

(vi) determining the ratio between the concentration of said p-xylene reference component and of said other component which is adsorbed; and (vii) determining the selectivity for said other component with respect to said p-xylene reference component by dividing the ratio of the concentration of said other component which is adsorbed to the concentration of said p-xylene reference component which is adsorbed by the ratio of the concentration of said other component in the equilibrium liquid to the concentration of said p-xylene reference component in the equilibrium liquid.

* * * * *

UNITED STATES PATENT AND TRADEMARK OFFICE
CERTIFICATE OF CORRECTION

PATENT NO. : 4,409,819

DATED : October 18, 1983

INVENTOR(S) : WILLIAM SMOLIN

It is certified that error appears in the above—identified patent and that said Letters Patent is hereby corrected as shown below:

Column 8, line 47 "produce" should be -- product --;
line 48 "paraxylene" should be -- para-xylene --;

Column 10, line 63 "Component" should be -- Composition --

Column 13, line 59 "1.09" should be -- 1.08 --

Column 21, line 62 "off" should be -- of --

Column 27, line 50 "23.28" should be -- 22.28 --

Signed and Sealed this

Twentieth Day of March 1984

[SEAL]

Attest:

GERALD J. MOSSINGHOFF

Attesting Officer

Commissioner of Patents and Trademarks